US010103762B1

(12) United States Patent
Bullington et al.

(10) Patent No.: US 10,103,762 B1
(45) Date of Patent: Oct. 16, 2018

(54) LIGHTING SYSTEM FOR MEDICAL APPOINTMENT PROGRESS TRACKING BY WI-FI DETECTION

(71) Applicants: Deborah T Bullington, Jackson, WY (US); Andrew B Bullington, Jackson, WY (US)

(72) Inventors: Deborah T Bullington, Jackson, WY (US); Andrew B Bullington, Jackson, WY (US)

( * ) Notice: Subject to any disclaimer, the term of this patent is extended or adjusted under 35 U.S.C. 154(b) by 0 days.

(21) Appl. No.: 15/439,792

(22) Filed: Feb. 22, 2017

(51) Int. Cl.
| | | |
|---|---|---|
| *H04B 7/00* | (2006.01) | |
| *H04B 1/38* | (2015.01) | |
| *H04L 12/26* | (2006.01) | |
| *H04L 29/08* | (2006.01) | |
| *F21V 33/00* | (2006.01) | |
| *G16H 40/20* | (2018.01) | |
| *H04W 84/12* | (2009.01) | |
| *F21W 131/20* | (2006.01) | |
| *G06Q 30/02* | (2012.01) | |

(52) U.S. Cl.
CPC ........... *H04B 1/38* (2013.01); *F21V 33/0052* (2013.01); *G16H 40/20* (2018.01); *H04L 43/106* (2013.01); *H04L 67/12* (2013.01); *F21W 2131/20* (2013.01); *G06Q 30/0282* (2013.01); *H04W 84/12* (2013.01)

(58) Field of Classification Search
CPC ......... H04B 1/38; H04W 84/12; G16H 40/20; G06Q 30/0282; F21V 33/0052; H04L 43/106; H04L 67/12

USPC ...................................... 455/90.1, 41.1, 41.2
See application file for complete search history.

(56) References Cited

U.S. PATENT DOCUMENTS

| | | | |
|---|---|---|---|
| 6,601,985 B1* | 8/2003 | Jesurun | F21S 2/00 |
| | | | 362/552 |
| 2008/0014868 A1* | 1/2008 | Davis | H04L 12/66 |
| | | | 455/41.2 |
| 2010/0123560 A1* | 5/2010 | Nix | H04Q 9/00 |
| | | | 340/10.4 |

* cited by examiner

*Primary Examiner* — Nhan Le
(74) *Attorney, Agent, or Firm* — Kwan & Olynick LLP

(57) ABSTRACT

Provided are mechanisms and processes for a lighting system for medical schedule management. According to various examples, an apparatus is provided which comprises a lighting interface configured to connect to a lighting element for illuminating a medical examination room. The apparatus further comprises a power interface coupled to a power source. The apparatus further comprises a Wi-Fi transceiver configured to transmit a wireless signal to connect to a device corresponding to a physician. The wireless signal corresponds to a local area network. The duration of the connection is used to track the presence of the physician in the medical examination room. The Wi-Fi transceiver is tuned to transmit a signal strength corresponding to the size and characteristics of the medical examination room. The apparatus is located in a lighting fixture in the medical examination room. The lighting fixture may be centrally located in the medical examination room.

20 Claims, 22 Drawing Sheets

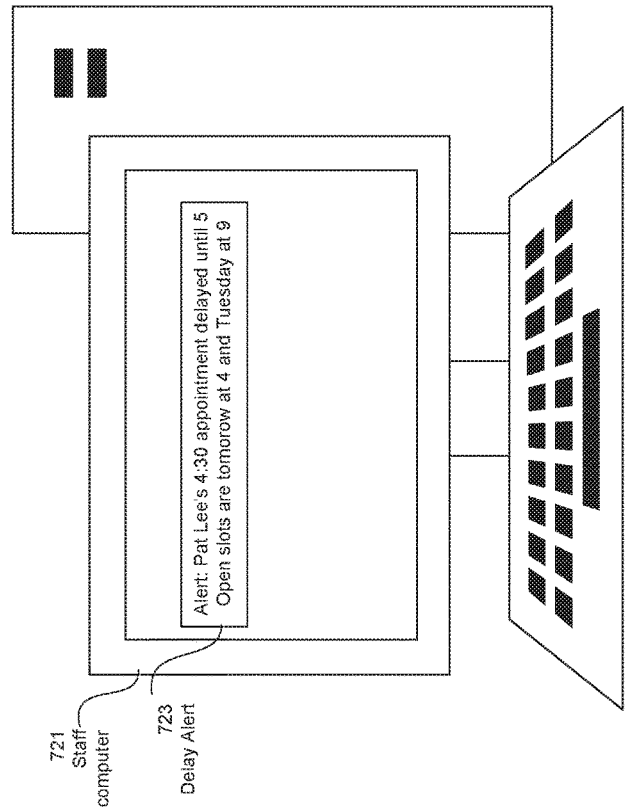
*FIG. 7C*
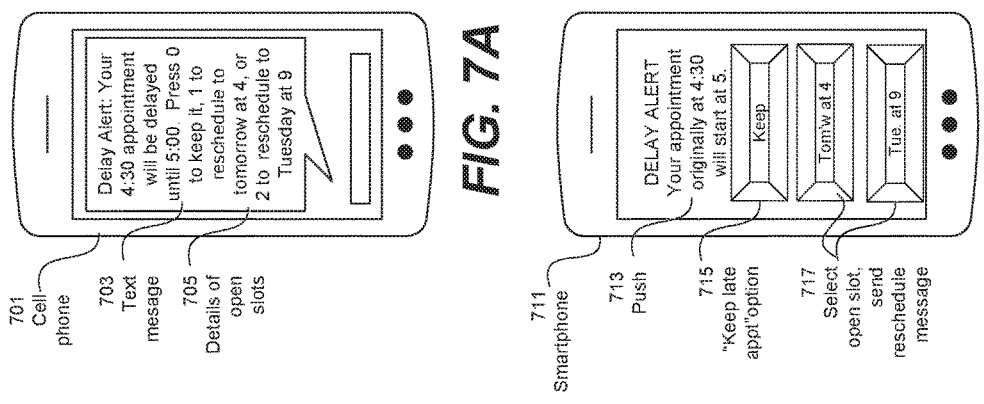
*FIG. 7A*
*FIG. 7B*

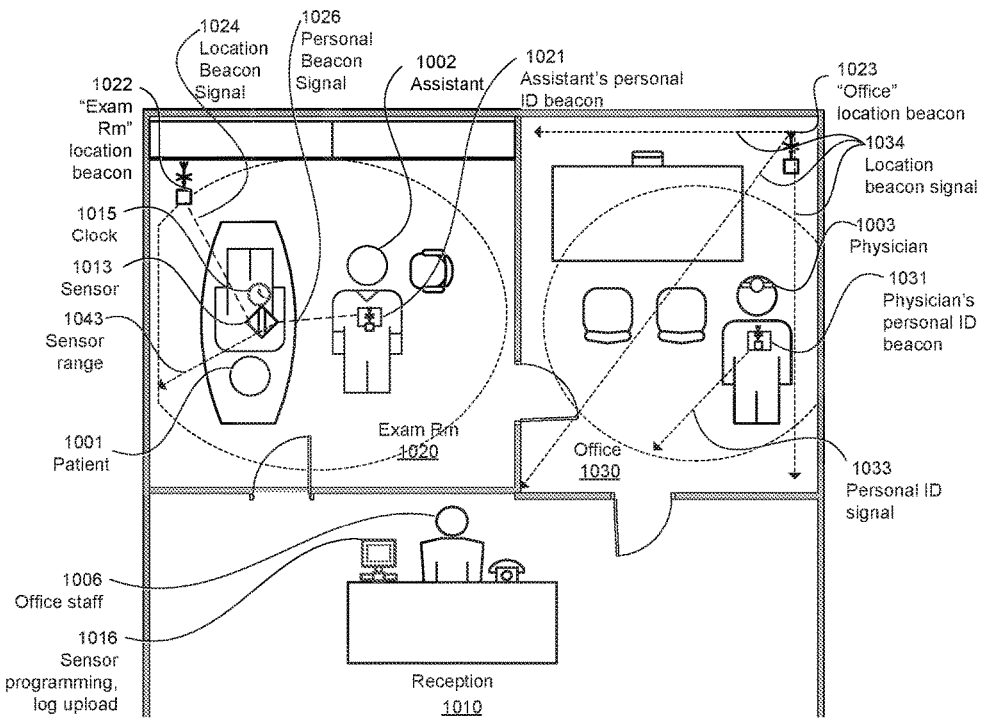
FIG. 10A
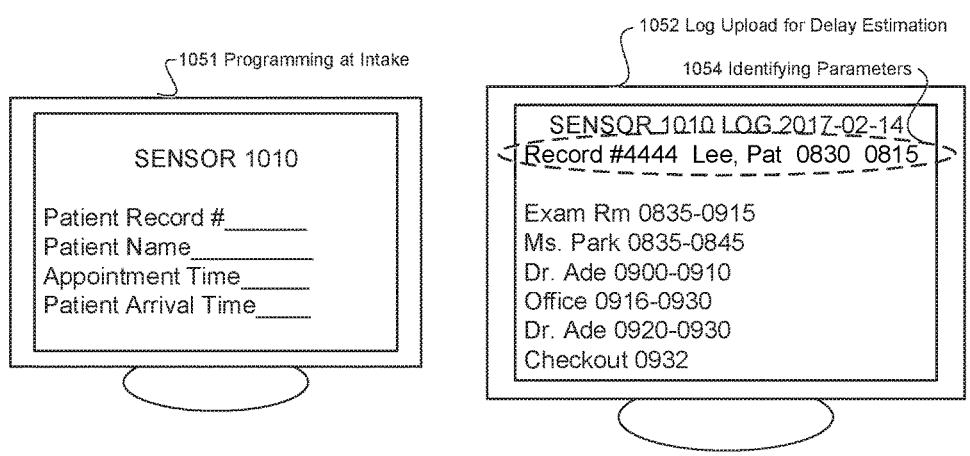
FIG. 10B  FIG. 10C

LIGHTING SYSTEM FOR MEDICAL APPOINTMENT PROGRESS TRACKING BY WI-FI DETECTION

BACKGROUND

Medical appointments are commonly associated with notoriously long wait times. According to numerous reviews from patients, the number one complaint is the wait time to see the doctor. For instance, online review sites allow patients to comment and provide corresponding star ratings for service providers. On these sites, low star ratings for physicians are often associated with comments citing long wait times. Often, reviewers complain of waiting from between thirty minutes to two hours. These reviews indicate that patient satisfaction with a physician's care can be heavily influenced by wait times, and that excessive wait times can lead to negative reviews of a physician's services.

Accordingly, improving the wait time for a patient can greatly improve the patient's satisfaction with the physician. In turn, this satisfaction will improve the patient's subjective feelings about their care, which can lead to more effective treatment and service. Specifically, when the patient is in a positive frame of mind at the beginning of the examination, the appointment naturally flows more smoothly. In addition, physicians often note that when they are behind schedule, they often spend time apologizing to the patient about being late, which reduces the amount of time available for actual patient care. By reducing or eliminating patient wait times, physicians can be more efficient and patients can have more positive experiences at appointments. Consequently, there is a need for improving patient wait times for medical appointments.

SUMMARY

Provided are various mechanisms and processes relating to an appointment scheduling management system. Although medical scheduling is used as a main example, those of ordinary skill in the art will recognize that the same problems may exist in any appointment-based service practice (including but not limited to dental, veterinary, legal, accounting, counseling, cosmetology, photography or auto repair concerns) and may accordingly be addressed by the subject matter of this disclosure.

In one aspect, which may include at least a portion of the subject matter of any of the preceding and/or following examples and aspects, an apparatus is provided which comprises a lighting interface configured to connect to a lighting element for illuminating a medical examination room. The apparatus further comprises a power interface coupled to a power source. The apparatus further comprises a Wi-Fi transceiver configured to transmit a wireless signal to connect to a device corresponding to a physician. The duration of the connection is used to track the presence of the physician in the medical examination room. The transceiver is tuned to transmit a signal strength corresponding to the size and characteristics of the medical examination room. The apparatus is located in a lighting fixture in the medical examination room. The lighting fixture may be centrally located in the medical examination room.

The Wi-Fi transceiver may be configured to transmit a plurality of multicast data packets to the device during the duration of the connection. Each multicast data packet may include information identifying the medical examination room. The Wi-Fi transceiver may be configured to receive a plurality of multicast data packets from the device during the duration of the connection. Each multicast data packet may include information identifying the corresponding physician.

The apparatus may be configured to log a timestamp based on the detected signal indicating the beginning of a first appointment. The apparatus may further be configured to compare the timestamp with scheduling information to predict whether future appointments will be delayed. Scheduling information may include a plurality of scheduled appointments which include the first appointment and a second appointment. Determining whether the second appointment will be substantially delayed includes comparing a second time associated with the second appointment with an originally scheduled time for the second appointment. The second time may be predicted based on an amount of delay from the first appointment. The apparatus may be further configured to notify a holder of the second appointment if the second appointment is determined to be substantially delayed.

In some embodiments, Wi-Fi transceiver may comprise a plurality of wireless routers. A first router may be configured to receive a wireless network signal corresponding to the network signal of the local area network. A second router may be configured to rebroadcast the wireless network signal as the wireless signal.

In other embodiments, the Wi-Fi transceiver may comprise a powerline adapter coupled to the power source via an electrical circuit. The powerline adapter may be configured to receive the network signal of the local area network over the electrical circuit and transmit the network signal as the wireless signal. The Wi-Fi transceiver and the lighting element may be electrically coupled in parallel.

Other implementations of this disclosure include corresponding methods, devices, systems, and computer programs, configured to perform the actions of the described method. For instance, a system is provided comprising a lighting fixture in a medical examination room, and a location tracker in the lighting fixture. The location tracker comprises a lighting interface configured to connect to a lighting element for illuminating the medical examination room. The location tracker further comprises a power interface coupled to a power source. The location tracker further comprises a Wi-Fi transceiver configured to transmit a wireless signal to connect to a device corresponding to a physician. The wireless signal may correspond to a local area network. The duration of the connection is used to track the presence of the physician in the medical examination room. The Wi-Fi transceiver is tuned to transmit a signal strength corresponding to the size and characteristics of the medical examination room. The lighting fixture may be centrally located in the medical examination room.

In another aspect, which may include at least a portion of the subject matter of any of the preceding and/or following examples and aspects, a method for appointment progress tracking is provided. The method comprises coupling a power interface of a lighting system to a power source. The lighting system may comprise a lighting fixture in a medical examination room. The lighting fixture may include a lighting interface configured to connect to a lighting element for illuminating the medical examination room. The lighting fixture may further include a Wi-Fi transceiver configured to receive a network signal of a local area network. The lighting fixture may be centrally located in the medical examination room.

The method further comprises transmitting, via the Wi-Fi transceiver, a wireless signal to connect to a device corresponding to a physician. The wireless signal corresponds to the network signal. The method further comprises tuning the signal strength of the wireless signal to correspond to the size and characteristics of the medical examination room.

In some embodiments, the Wi-Fi transceiver may comprise a plurality of wireless routers. A first router may be configured to receive a wireless network signal corresponding to the network signal of the local area network. A second router may be configured to rebroadcast the wireless network signal as the wireless signal. In some embodiments, the Wi-Fi transceiver may comprise a powerline adapter coupled to the power source via an electrical circuit. The powerline adapter may be configured to receive the network signal of the local area network over the electrical circuit and transmit the network signal as the wireless signal. The Wi-Fi transceiver and the lighting element are electrically coupled in parallel.

The method further comprises tracking the presence of the physician in the medical examination room based on the duration of the connection. In some embodiments, the method further comprises transmitting, via the Wi-Fi transceiver, a plurality of multicast data packets to the device during the duration of the connection. Each multicast data packet may include information identifying the medical examination room. In further embodiments, the method further comprises receiving a plurality of multicast data packets from the device during the duration of the connection. Each multicast data packet may include information identifying the corresponding physician.

The method further comprises logging a timestamp based on the duration of the connection indicating the duration of a first appointment. The timestamp may be compared with scheduling information to predict whether future appointments will be substantially delayed. Scheduling information may include a plurality of scheduled appointments, which include the first appointment and a second appointment. The method may further comprise notifying a holder of the second appointment if the second appointment is determined to be substantially delayed.

These and other embodiments are described further below with reference to the figures.

BRIEF DESCRIPTION OF THE DRAWINGS

FIGS. 7A-7C illustrate examples of user interface screens for the appointment management system.

FIGS. 10A-10C are diagrams illustrating one example of a system in which sensors are worn by patients and identifier beacons are worn by employees and placed in service locations.

DETAILED DESCRIPTION OF EXAMPLE EMBODIMENTS

Figure 1:
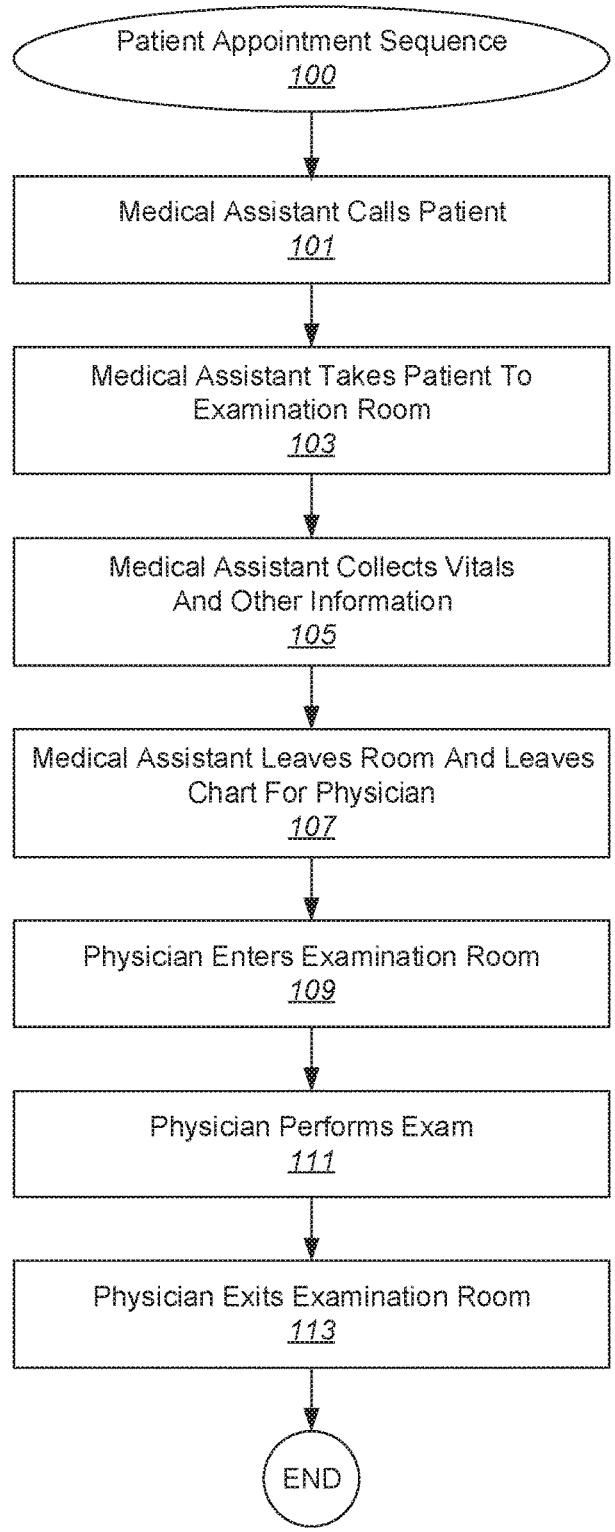
FIG. 1 is a flow chart illustrating one example of a patient appointment sequence.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques of the present invention will be described in the context of particular scheduling mechanisms for medical offices. However, it should be noted that the techniques of the present invention apply to a wide variety of different scheduling mechanisms for a variety of different types of service entities such as dental offices, vision service providers, etc., or other non-medical service entities, such as automotive repair, dog grooming, etc. As another example, the techniques of the present invention will be described in the context of particular wireless signals, such as Wi-Fi. However, it should be noted that the techniques of the present invention apply to a wide variety of different wireless signals, including Bluetooth, infrared, light of sight transmission mechanisms, as well as various other networking protocols.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Medical appointments are commonly associated with notoriously long wait times. Because patient satisfaction with a physician's care can be heavily influenced by wait times, excessive wait times can lead to negative reviews of a physician's services. By reducing or eliminating patient wait times, physicians can be more efficient and patients can have more positive experiences at medical offices. The same applies to other providers of services by appointment whose schedules may be subject to delays for various reasons.

Accordingly, various embodiments of the present invention address the issue of wait times in medical offices. In some examples, a physician's progress is monitored and any delays in the physician's schedule are detected. Patients are then informed of any delays or schedule changes in real-time. Specifically, a medical scheduling management system tracks the physician's progress and provides notifications, such as through text messages, to upcoming patients. These notifications can let patients know when a physician is running behind and ask them to arrive later than their originally scheduled appointment.

By notifying patients in real-time about schedule changes or fluctuations, the intent is to decrease the amount of time that each patient waits for their appointment to begin. In turn, reducing the wait time should increase patient satisfaction and result in more positive experiences with their physicians. Because reimbursement according to programs like Medicare will be highly dependent on patient satisfaction in the future, the amount physicians will be paid will be closely tied to their patients' satisfaction. By keeping patients informed of schedule status and changes, the system described in various examples of this disclosure has the potential to address one of the biggest problems with patient satisfaction: wait times. If patient satisfaction is increased, then there is a higher likelihood that physicians will be fully reimbursed for their work. In addition, higher patient satisfaction will also lead to more referrals from patients and more business for physicians.

According to various embodiments, physician and other service employee activities, movements, and locations can be automatically or manually detected to allow improved appointment scheduling. For example, appointment start times can be manually or automatically triggered when a physician enters or a room and characteristics of the appointment can be used to determine whether later appointments need to be adjusted.

According to various embodiments, a transceiver such as a Bluetooth or Wi-Fi transceiver is integrated into a lighting system centrally located in a medical office. In some embodiments, the transceiver is integrated into a light bulb and is tuned to transmit at a signal strength corresponding to the size of the medical office. It is recognized that using Bluetooth or Wi-Fi is effective for roughly tracking medical personnel location. However, signals leak into hallways and into other rooms, and a Bluetooth or Wi-Fi acknowledgment signal received from a medical personnel device such as a smartphone or other location tracker may only be somewhat reliable.

Various embodiments of the present invention recognize that having Bluetooth or Wi-Fi transceivers in each medical office in a centrally located, easily maintained lighting fixture allows medical personnel movement to be more easily tracked. A Bluetooth signal detected at a transceiver in a first medical office will be several times stronger if a doctor is in the first medical office than if the doctor is in a different medical office. Various protocols could be used including various flavors of Bluetooth, Wi-Fi, light of sight transmission mechanisms, as well as other networking protocols. According to various embodiments, the transceiver may operate as a Bluetooth or Wi-Fi booster or repeater.

Furthermore, with a transceiver centrally located in an examination room, a wireless signal with a uniform signal strength may be transmitted to cover the examination room. However, directionality of wireless signals may be implemented to provide fencing of such wireless signals by creating an aggregated signal with a signal range of a particular shape corresponding to the room. Thus, a centrally located wireless transceiver may provide a more accurate indicator of when a particular individual is within a particular room.

As such, a transceiver may be integrated into the lighting system in a room, such as an examination room. In some embodiments, the transceiver is integrated into a light fixture. In another embodiment, the transceiver is integrated into a light bulb. In still other embodiments, the transceiver is an adapter that attaches on one end to a conventional lighting fixture and on the other end to a conventional light bulb. In this way, the transceiver becomes a centrally located device with access to continuous power. Integrating the transceiver into a lighting system incorporates the transceiver and/or tracking system into an essential structure of the exam room, which may reduce clutter in an exam room in which limited space may already be designated for various tools, furniture, and other essential appliances. In various embodiments, the lighting element of the lighting system, such as wire filaments and/or diodes, may function as an antenna for transmission and reception of wireless signals.

Additionally, a transceiver may be integrated into a lighting system which may be adjusted by a medical professional (such as a physician or medical assistant) to illuminate a patient and/or a particular area of the patient. Thus, in various examples, the position of lighting system may closely correspond to the location of a patient, medical professional and/or other individual or user. In this way, the proximity of an individual to lighting system may indicate when an examination has begun or is in progress.

Software applications may assist technicians in tuning the needed strength of the transceivers in the light fixtures including light bulbs based on the size and characteristics of the room. According to various embodiments, medical personnel are not required to login, check in, or do any extra work to indicate their presence in a room. Instead, medical personnel location is tracked based on the signals received at the various Bluetooth or Wi-Fi transceivers.

Constraining the wireless signal to the size and characteristics of the room may also provide additional advantages in privacy protections for sensitive private medical information protected under the federal Health Insurance Portability and Accountability Act of 1996 (HIPAA). For example, the location tracking system may not be subject to unauthorized access by devices not within the examination room, reducing the risk of unauthorized access to sensitive medical information. Furthermore, unique identification codes may be used to determine location, which is further separated from patient appointment information, and further separated from patient medical records.

In some embodiments, the transceiver may function as a Wi-Fi extender (also referred to herein as a Wi-Fi booster or repeater). A Wi-Fi extender may be configured to directly and/or wirelessly connect to an existing network signal and rebroadcast the signal wirelessly into the room. In some embodiments, the network signal may be transmitted to the Wi-Fi extender via electrical currents in an electrical circuit. Thus, the same electrical current may provide power to the lighting system, as well as the signal to be broadcasted. In some embodiments, the signal may be broadcasted through lighting elements, such as wire filaments or diodes.

Once a user device has connected with the rebroadcasted signal, information within transmitted data packets may be used to identify the room location and/or duration of the connection. Additionally, and/or alternatively, information within data packets transmitted by a connected user device may be used to identify the individual corresponding to the user device and/or duration of the connection.

This disclosed system may be implemented on a secure network to further provide additional advantages in privacy protections for sensitive private medical information protected under HIPAA. For example, user devices may not be authorized to connect to the secure network. However, multicast data packets may still be sent and/or received between the Wi-Fi extender and user devices to indicate a connection, as well as to identify the corresponding individual and/or room location. Such information may be stored in other portions of a multicast data packet, such as the source IP address or MAC addresses. In this way, the location and identity of an individual, as well as the duration of the connection, may be identified without any access to the secure network by the user device.

In particular embodiments, mechanisms for tracking physician or other medical personnel activities, movements, and locations for scheduling appointments are firewalled from systems managing patient medical data. In some examples, different encryption mechanisms are used to encode patient medical data and medical personnel scheduling data so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

With reference to FIG. 1, shown is a flow chart illustrating one example of a patient appointment sequence. As shown, a typical patient appointment sequence 100 begins when a medical assistant (or nurse in some cases), calls a patient at 101 from the waiting room. Various embodiments will be described with reference to particular medical personnel. However, it should be noted that numerous activities can be performed by a variety of different medical professionals such as medical staff, medical assistants, nurses, physician assistants, physicians, residents, etc. A variety of triggers can also be used to initiate scheduling mechanisms, such as when a physician enters the patient's examination room, when a physician leaves the patient's examination room, when a nurse brings a patient to an examination room, etc.

According to various embodiments, a medical assistant then takes the patient to the examination room at 103. During the medical assistant's session with the patient, the medical assistant often collects information such as vitals and other data at 105. This may include aspects such as measuring temperature, blood pressure, and the like. In addition, this process can include weighing and measuring the height of the patient. In some cases, these measurements may be taken in a hallway on the way to the examination room. The medical assistant may also ask the patient questions and take notes. The medical assistant then leaves the examination room and leaves the patient's chart for the physician. The patient is then left alone in the examination room to wait for the physician. This time may also be used for changing into a gown, etc.

Next, the physician enters the examination room at 109. The physician performs the exam at 111, and then exits the examination room at 113. This concludes the process and the patient changes clothes, if appropriate, and collects their belongings before leaving the examination room.

As described, a medical appointment includes various phases that may include wait times. For instance, the patient may wait for a period of time before the medical assistant initially calls the patient at 101. The patient may also wait for a period of time between the time the medical assistant leaves the room at 107 and the time the physician enters the room at 109. Both of these wait times affect patient satisfaction and can lead to complaints relating to patient care. In addition, the amount of time that a physician spends with a particular patient, between blocks 109 and 113, affects whether future appointments that day will be on time or delayed. Accordingly, the timing of various phases of a patient appointment sequence can affect patient satisfaction and determine whether future appointments will be delayed.

FIGS. 2A-2E are diagrams illustrating one example of a system of sensors, identifiers, and their signals.

Figure 2A:
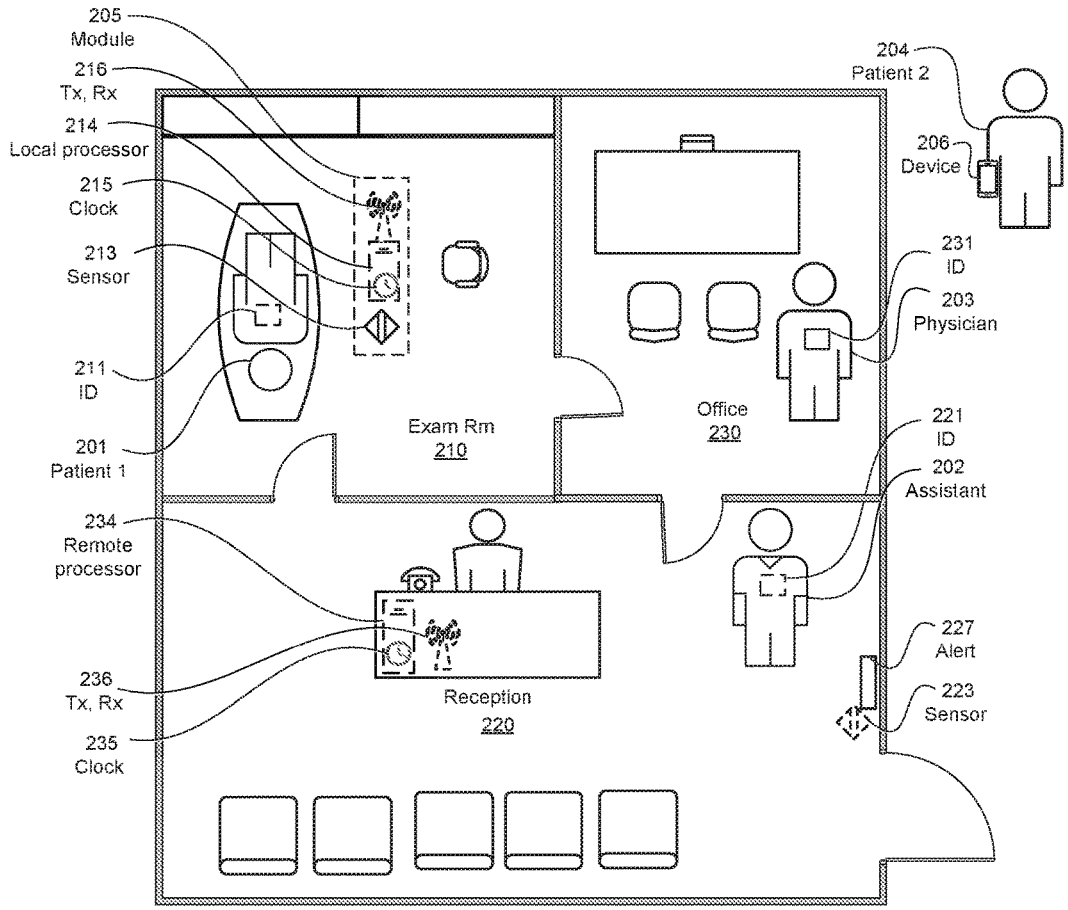
FIGS. 2A-2E are diagrams illustrating one example of a system of sensors, identifiers, and their signals.

With reference to FIG. 2A, shown is an example of a partial medical-office floor plan with an example of the system installed. Physician 203, shown in office 230, is the wearer of physician's identifier 231. Physician's identifier (ID) 231 may be an active beacon or a non-powered readable tag such as an RFID or infrared tag. In this example, office 230 does not have any sensors; for example, it may be used for purposes that do not involve the presence of patients.

In some embodiments, only the physician might wear an ID if his or her availability primarily affects a patient's waiting time. If more than one person wears an identifier, each of the identifiers may optionally expose or transmit a unique parameter. The parameter may include the wearer's role ("Doctor"), name ("Dr. Smith"), or any other encodable information linking the detected ID with its wearer. Such identification parameters allow the sensor to record who is entering or exiting a service location as well as when they enter or exit.

In some embodiments, assistant 202 also wears an ID, distinguishable by the sensor(s) as assistant's identifier 221. As illustrated, assistant's identifier 221 may be in position to be detected by door sensor 223 in waiting room 220. Door sensor 223 may activate door alert 227 to keep patients from inadvertently leaving with their IDs. Alternatively, door sensor 223 may simply record entry and exit of ID-wearers through the main office door. Door sensor 223 is logged by remote processor 234, which has a dedicated clock 235 and transmitter/receiver 236. In some embodiments, remote processor 234 is a hub processor for multiple sensors.

Patient 201, who has the current appointment, waits in service location 210, an exam room. Optionally, patient 201 may wear a patient's identifier 211. Patient ID 211 may help locate the patient in the office if there is any confusion about where he or she is. Logging patient ID 211's interactions with door sensor 223 may also isolate the variable of patient arrival time if the sensor data on appointment timing is to be analyzed.

Also in exam room 210 is an exam-room sensor 213. As illustrated, exam-room sensor 213 is part of a self-contained sensor module 205, another optional configuration for location sensors. Also in sensor module 205 are dedicated sensor processor 214, dedicated clock 215, and sensor transmitter/receiver 216.

Delays and other events logged by sensors may trigger alerts on office employees' devices (mobile or not). For practices that emphasize human contact, that notification may be sufficient; an employee would then personally contact a patient with a delayed upcoming appointment and explain options. By contrast, in a practice that prefers to reach patients via technology may use an embodiment that sends scheduling updates to device 206 accessed by upcoming patient 204, a holder of a later appointment.

Figure 2B:
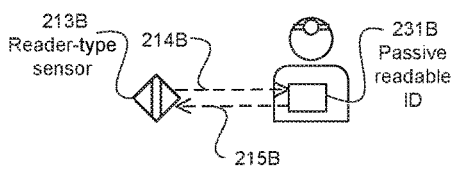

With reference to FIG. 2B, shown is a diagram of detection of a passive readable ID. ID 231B does not have its own power source. Sensor 213B emits signal 214B, which impinges on ID 231B and is returned as return signal 215B. For example, ID 231B may be an RFID tag that, when within range of sensor 213B, takes power 214B from sensor 213B and uses it to emit its own signal 215B for detection by sensor 213B. In some embodiments, sensor 213B may emit signal 214B as pulses in predetermined intervals to periodically check for a return signal 215B. As long as ID 231B is in range, a return signal 215B will be periodically sent to the sensor 213B. By emitting a signal 214B in interval pulses may result in reduced power used as compared to emitting a continuous signal.

As another example, ID 231B may be a bar or QR code and sensor 213B may include a scanning laser. The laser beam 214B (e.g., an eye-safe low-power infrared laser) is reflected or scattered from a coded pattern (e.g., a barcode or QR code) on ID 231B. The reflected or scattered light goes back to sensor 213B as return signal 215B. In some embodiments, sensor 213B may emit laser beam 214B in predetermined intervals. As long as a return signal 215B is detected by sensor 213B at a regular interval, it can be determined that the ID 231B is within range. By emitting laser beam 214B in predetermined intervals may result in reduced power used as compared to emitting a continuous signal.

Figure 2C:
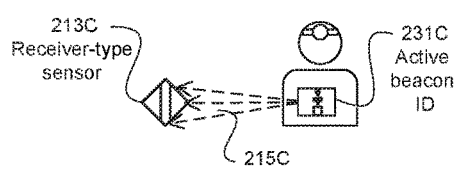

With reference to FIG. 2C, shown is a diagram of detection of an emitted signal from an active beacon ID. ID 231C may have its own power source enabling it to independently emit signal 215C toward sensor 213C. In some embodiments, ID 231C may emit signal 215C toward sensor 213C in pulses at predetermined intervals. As long as a signal is detected by sensor 213C at a regular interval, it can be determined that the ID 231C is within range. By emitting a signal in interval pulses may result in reduced power used as compared to emitting a continuous signal.

For example, beacons available at the time of this writing have dimensions on the order of 5-10 cm (2-4"), weights of less than 1 ounce, and line-of-sight ranges of a few centimeters to a few hundred meters, depending partially on whether their signals are Bluetooth™, Bluetooth Low Energy (BTLE)™, ANT+™, IEEE 802.22™, IrDA™, NFC™, RFID™, Wi-Fi™, ZigBee™, wireless USB or HART, or some other signal type. Some active beacons have built-in sensors for motion, light, magnetic fields, heat, and other quantities. A beacon with a built-in sensor could potentially function as either a beacon or a sensor, so that only one type of unit needs to be ordered, deployed, and tracked. Some active beacons with built-in processors and memory may be reprogrammed to change their signal characteristics, either to uniquely identify particular beacons or to avoid interference with medical equipment. Such beacons may, for example, be shared by employees whose shifts do not overlap or patients whose appointments do not overlap. In either case, beacon 231C may be reprogrammed between uses to transmit the identifying parameter of the next wearer rather than the preceding one.

In some embodiments, ID 231C may comprise a user device, such as medical professional mobile device 1301, further described below. In some embodiments, sensor 213C may emit signal 215C toward ID user device 231C. Upon detecting signal 215C, device 231C may determine that the ID 231C is within range of sensor 213C. In some embodiments, sensor 213C may emit signal 215C toward ID 231C in pulses at predetermined intervals. As long as a signal is detected by ID 231C at a regular interval, it can be determined that the ID 231C is within range. By emitting a signal in interval pulses may result in reduced power used as compared to emitting a continuous signal.

Figure 2D:
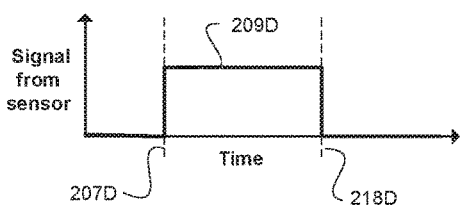

With reference to FIG. 2D, shown is one type of sensor signal from which entry and exit times may be derived. The sensor emits a signal 209D as long as it detects an ID in range, and emits no signal (at least, no signal associated with that particular ID) while the ID is out of range. The processor will read upward transition 207D as an entry and downward transition 218D as an exit.

In some embodiments, the sensor may emit a pulse at a predetermined interval as long as it detects an ID in range. For example, the sensor may periodically check for an ID at the predetermined interval and emits a pulse if an ID is detected. As long as a pulse is emitted at a regular interval, it can be determined at the processor that the ID is within range. If no ID is detected, then no pulse is emitted and the regular interval of emitted pulses will be broken and it can bet determined that the ID is no longer within range. By emitting a signal in interval pulses may result in reduced power used as compared to emitting a continuous signal.

Figure 2E:
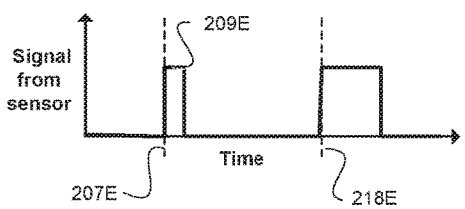

With reference to FIG. 2E, shown is another type of sensor signal from which entry and exit times may be derived. The sensor sends a first pulse 209E at time 207E when an ID comes within the sensor's range, emits no signal associated with that particular sensor while it remains in range, then emits a second pulse at time 218E in response to the ID moving out of the sensor range. In some embodiments, it may be preferable to conserve beacon power; this schema uses significantly less power than emitting a signal continuously as in FIG. 2D. Distinguishing between entry and exit may be done via pulse length, as here, but alternatively by frequency, number of pulses, attack/release waveform, or the like.

Figure 3:
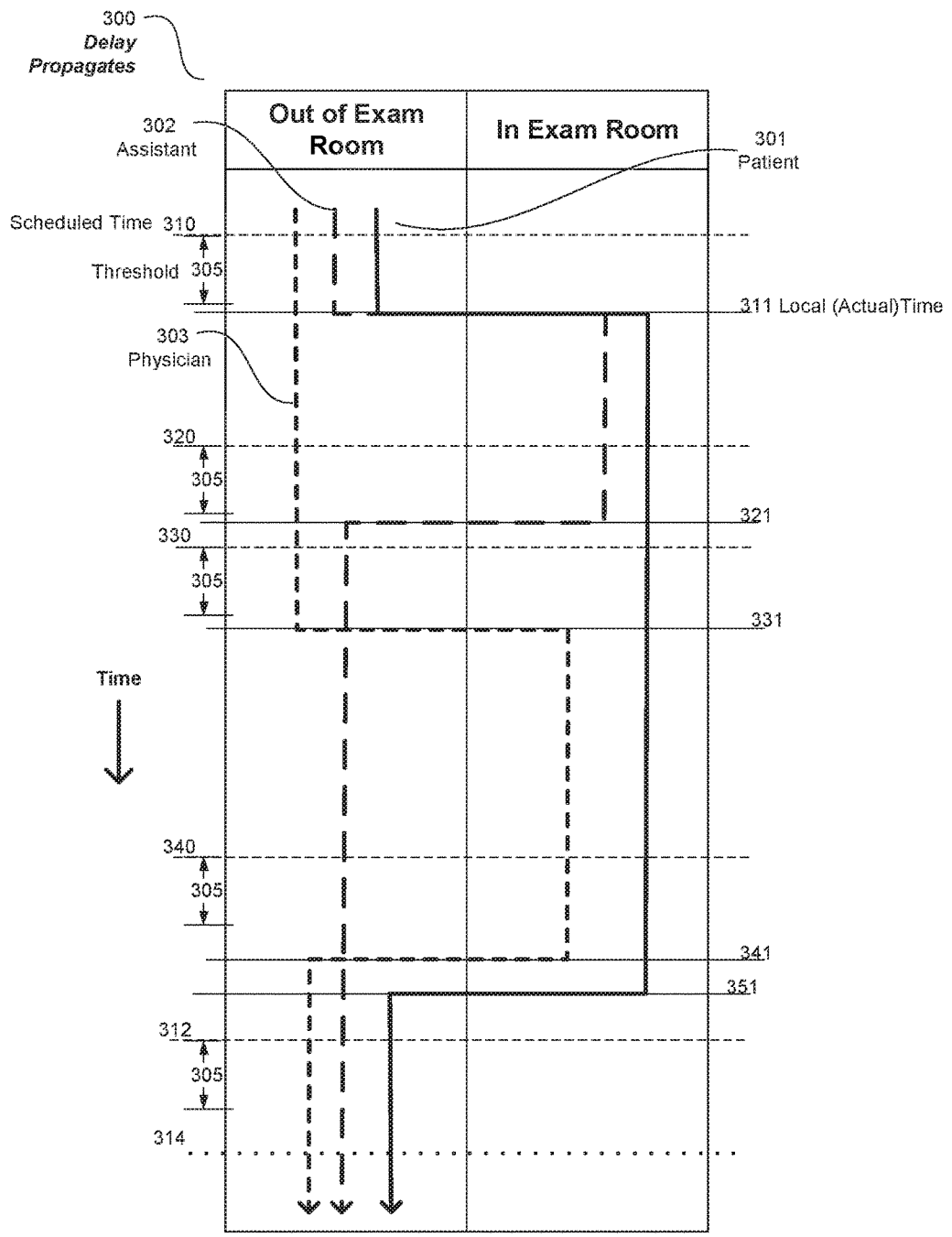
FIG. 3 is a swim-lane diagram of propagating delays of appointments.

With reference to FIG. 3, shown is a swim-lane diagram of propagating delays in appointments. This figure graphically represents the appointment routine described with reference to FIG. 1. A single sensor in the exam room monitors the progress of the appointment. At time 311, the assistant (long-dash line 302) brings the patient (solid line 301) into the exam room. After some time taking vital signs and the like, assistant 302 leaves the exam room at time 321, leaving patient 301 in the exam room waiting for the physician. The physician (short-dash line 303) enters the exam room at time 331, performs the exam, and leaves at time 341.

Horizontal fine solid lines 311, 321, 331, 341 and 351 represent local times logged when actual entries or exits are detected. Therefore, they coincide with times at which the thicker lines representing the locations of physician 303, assistant 302, and patient 301, cross between the "Out of Exam Room" lane (i.e., out of the detection range of an exam-room sensor) and the "In Exam Room" line (i.e., in the detectable range of the exam-room sensor). By contrast, horizontal fine dotted lines 310, 320, 330, and 340 represent the scheduled entry and exit times. These times are stored in advance when the day's schedule is prepared, then retrieved to calculate a delay after each corresponding actual entry or exit occurs. For example, assistant 302 was scheduled to escort the patient into the exam room at time 310, but did not actually do so until time 311; the appointment is already running behind schedule.

In this example, delays propagate: every subsequent delay is either the same length or longer than the immediately previous delay. Besides computing the delay between the scheduled and actual events, some embodiments of the process compare the delay to a stored threshold 305. Thresholding prevents excess notifications of employee and patient devices when the delay is deemed too small to cause patients of employees to change his or her plans. Digital clocks can measure delays of tiny fractions of a second, but humans, depending on the situation, may consider delays of less than a few minutes—or even delays of less than ½ hour—too small to warrant rescheduling the appointment. Setting a threshold 305 allows employees and upcoming patients to go about their day without being distracted by alerts about delays too small to cause concern.

Figure 4A:
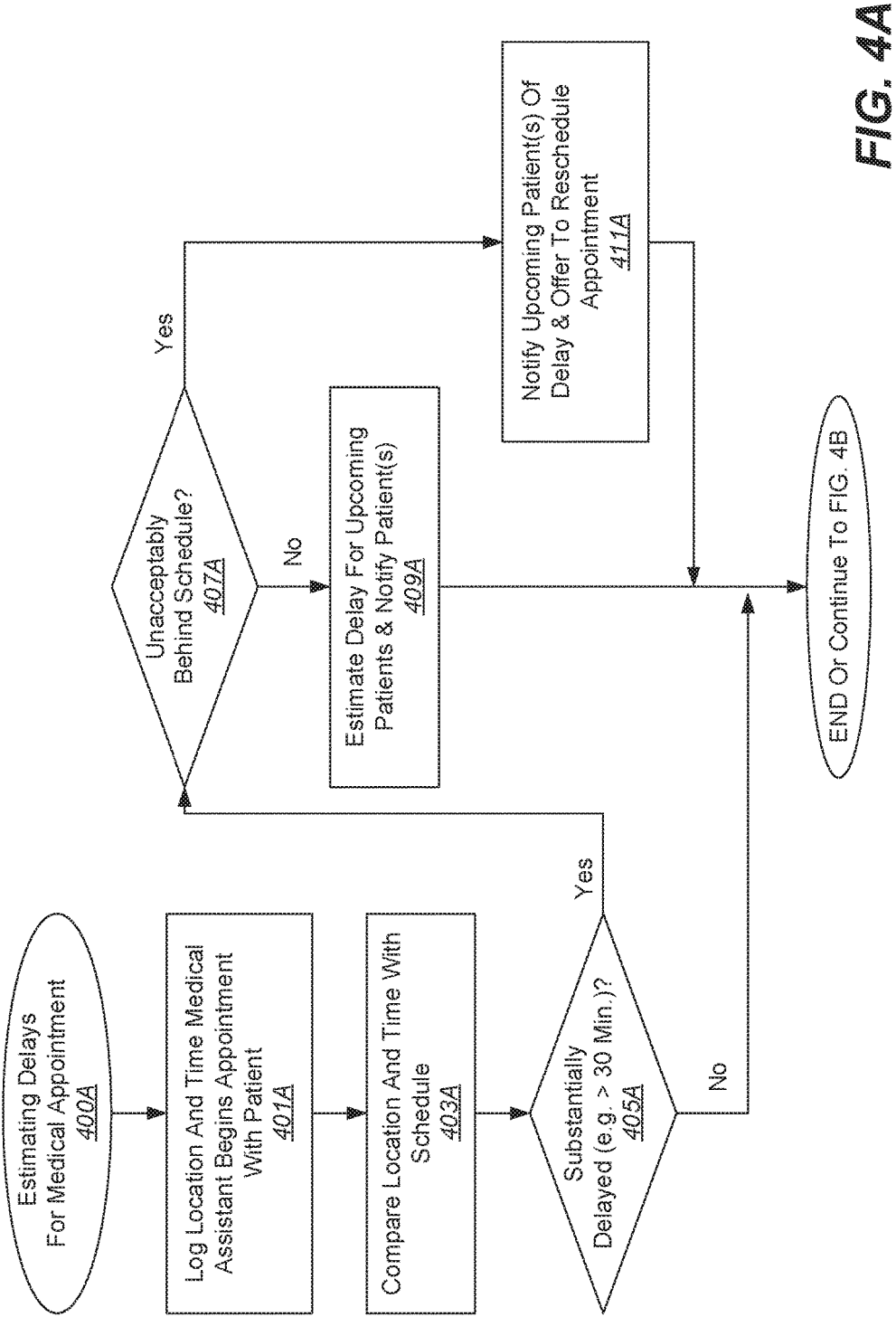
FIGS. 4A-4C are flow sequences illustrating one example of a process for estimating delays for a medical appointment.
Figure 4B:
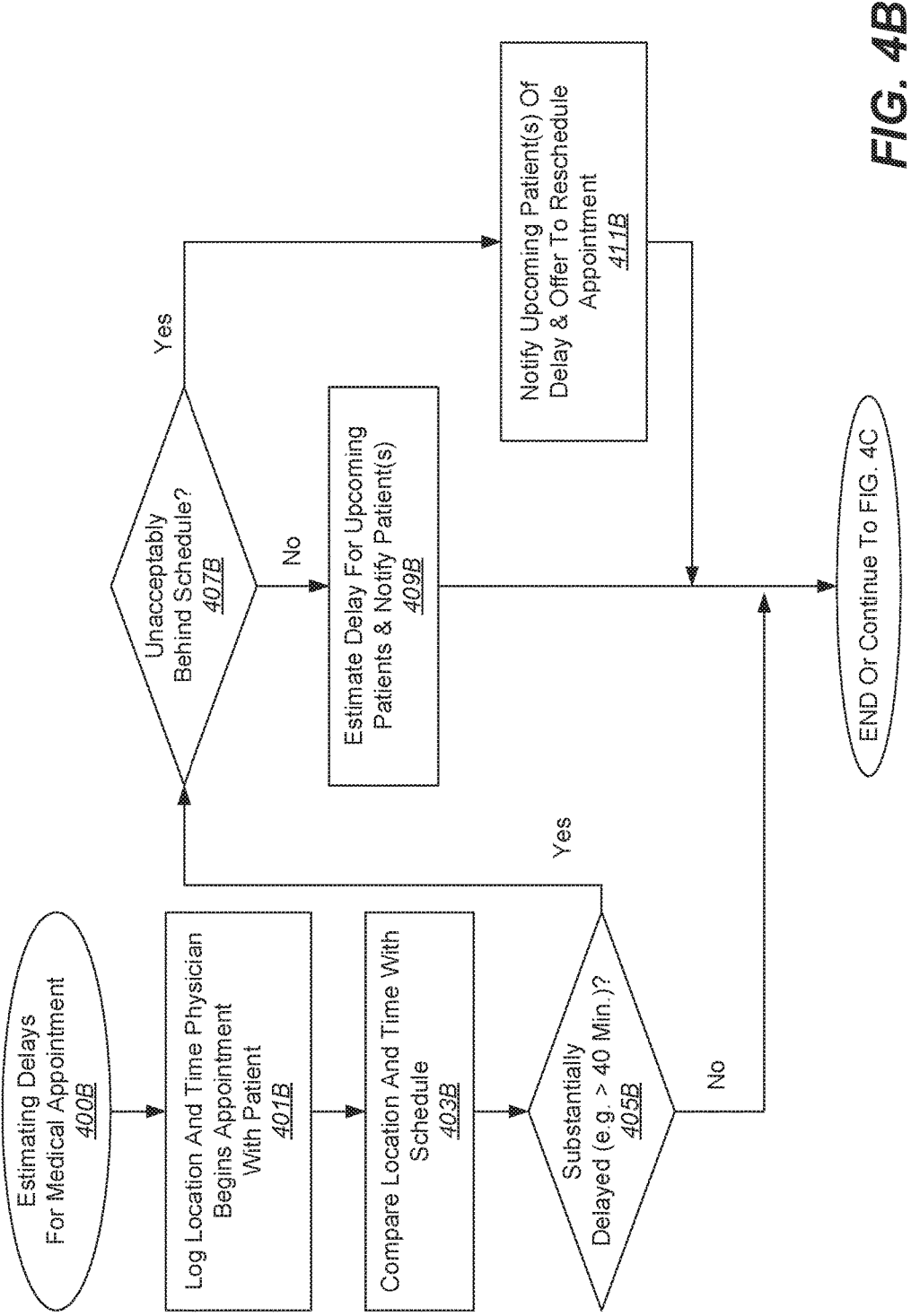
Figure 4C:
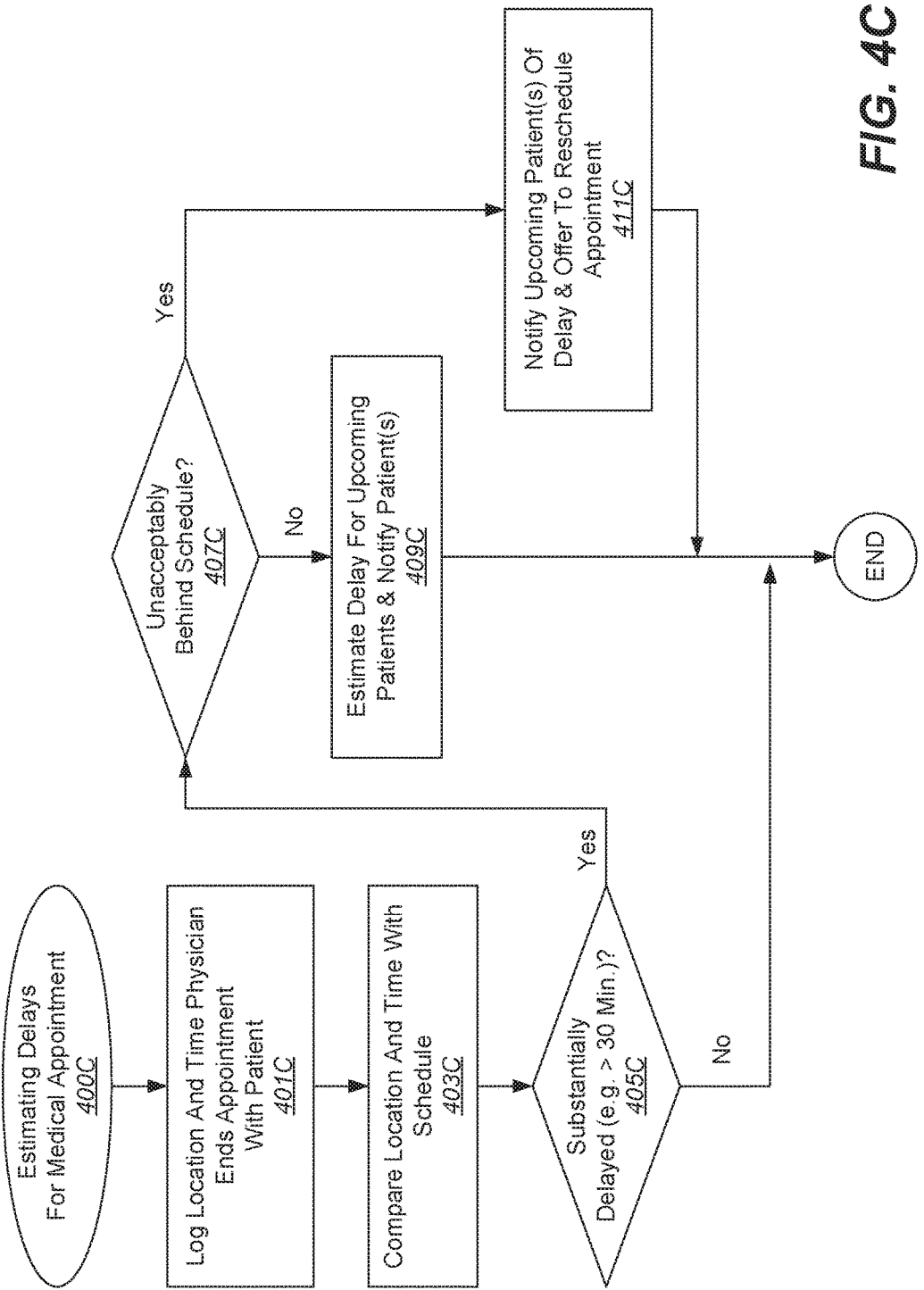

FIGS. 4A-4C illustrate examples of flow sequences of processes for estimating delays for a medical appointment. The processes shown in each of the figures can be used alone or together, depending on the application. For instance, the process shown in FIG. 4A can be used alone in some examples, whereas, FIGS. 4A-4C can be combined in other examples. In some aspects, the notification system can be viewed as a virtual waiting room. The system tracks when appointments are running late and the system informs an upcoming patient that their appointment is delayed and that they should delay arrival by a certain amount of time.

With reference to FIG. 4A, shown is a flow sequence illustrating one example of a process for estimating delays for a medical appointment. In this example, delays in the schedule are estimated based on the time that a medical assistant (or nurse) begins an appointment with a patient. According to various embodiments, scheduling times, activity and location tracking, event monitoring, and other triggers pertinent to maintaining on-time scheduled appointments are referred to herein as scheduling information. In this process, estimating delays for a medical appointment 400A begins with logging a location and time when a medical assistant begins an appointment with a patient at 401A. Next, this logged location and time is compared to a schedule at 403A. This schedule includes the patients and times for their appointments for the current day. Based on this comparison, a determination is made whether the appointment is on time or substantially delayed at 405A. For instance, if the time that the medical assistant begins the appointment is less than thirty (30) minutes later than the scheduled time for this patient, the appointment can be categorized as being on time and the process ends. If the time that the medical assistant begins the appointment is thirty (30) minutes or more past the scheduled time for this patient, then the appointment can be considered to be substantially delayed and the process continues at 407A. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407A. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled, any amount of time can be used depending on the particular application of the system. For instance, certain physicians may want to decrease this time based on their allotted examination times or to generally increase patient satisfaction.

In the current example, if the delay is less than two (2) hours, then delays for upcoming appointments are then estimated and these upcoming patients are notified of these delays at 409A. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified.

According to various embodiments, upcoming patients are notified at 409A using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA) or similar medical privacy laws in other nations. Specifically, the notification system accesses the contact information for upcoming patients, such as a phone number. In some examples, the notification system sends a text message to the upcoming patients notifying them of the expected delay and a later time that they should arrive. For instance, an upcoming patient originally scheduled for a two o'clock appointment may receive the following message: "Dear Jane, your appointment originally scheduled for 4:00 pm today with Dr. Smith is running behind schedule. Could you please arrive at 4:45 pm instead? Sorry for the delay. Thank you for your understanding." Alternatively, the notification system can send a voicemail or email to upcoming patients, depending on factors such as the patients' contact preferences and the office infrastructure. According to various embodiments, scheduling information such as medical professional location tracking, appointment start triggers, event monitoring, etc., are cryptographically separated from HIPAA information.

According to various embodiments, medical professional activities, movements, and locations can be automatically or manually detected to allow improved appointment scheduling. For example, appointment start times can be manually or automatically triggered when a physician enters or a room and characteristics of the appointment can be used to determine whether later appointments need to be adjusted. In particular embodiments, mechanisms for tracking physician or other medical personnel activities, movements, and locations for scheduling appointments are firewalled from systems managing patient medical data. In some examples, different encryption mechanisms are used to encrypt HIPAA data and scheduling information so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

In the present example, if the delay is two (2) hours or more, then a determination is made whether some or all of the upcoming patients for the day need to be rescheduled. The patients that need rescheduling are then notified at 411A and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the described process (or if no delay is found), the process either ends or continues as described in FIG. 4B, depending on the desired application of the system.

With reference to FIG. 4B, shown is a flow sequence illustrating another example of a process for estimating delays for a medical appointment. In this example, delays in the schedule are estimated based on the time that a physician begins an appointment with a patient. This process can be used alone in some examples, or it can continue following the process described above with regard to FIG. 4A.

In the present example, estimating delays for a medical appointment 400B begins with logging a location and time when the physician begins an appointment with a patient at 401B. Next, this logged location and time is compared to a schedule at 403B. This schedule includes the patients and times for their appointments for the current day. Based on this comparison, a determination is made whether the appointment is on time or substantially delayed at 405B. For instance, if the time that the physician begins the appointment is less than thirty (30) minutes later than the scheduled time for this patient, the appointment can be categorized as being on time and the process ends. If the time that the physician begins the appointment is thirty (30) minutes or more past the scheduled time for this patient, then the appointment can be considered to be substantially delayed and the process continues at 407B. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407B. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 409B. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 409 using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA). Specifically, the notification system accesses the contact information for upcoming patients, such as a phone number. In some examples, the notification system sends a text message to the upcoming patients notifying them of the expected delay and a later time that they should arrive. For instance, a patient later in the day scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled. The patients that need rescheduling are then notified at 411B and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the process (or if no delay is found), the process either ends or continues as described in FIG. 4C, depending on the desired application of the system.

In the present example, although both a location and time are logged when the physician begins the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing.

With reference to FIG. 4C, shown is a flow sequence illustrating another example of a process for estimating delays for a medical appointment. In this example, delays in the schedule are estimated based on the time that a physician ends an appointment with a patient. This process can be used alone in some examples, or it can continue following the process described above with regard to FIGS. 4A and/or 4B.

In the present example, estimating delays for a medical appointment 400C begins with logging a location and time when the physician ends an appointment with a patient at 401C. Next, this logged location and time is compared to a schedule at 403C. This schedule includes the patients and times for their appointments for the current day. Based on this comparison, a determination is made whether the appointment is on time or substantially delayed at 405C. For instance, if the time that the physician ends the appointment is less than thirty (30) minutes later than the scheduled time for this patient plus the allotted duration of this type of appointment, the appointment can be categorized as being on time and the process ends. If the time that the physician ends the appointment is thirty (30) minutes or more past the scheduled time for this patient plus the allotted duration of this type of appointment, then the appointment can be considered to be substantially delayed and the process continues at 407C. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407C. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 409C. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and/or the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 409C using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA). Specifically, the notification system accesses the contact information for upcoming patients, such as a phone number. In some examples, the notification system sends a text message to the upcoming patients notifying them of the expected delay and a later time that they should arrive. For instance, an upcoming patient scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled. The patients that need rescheduling are then notified at 411C and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through a text message, email, voice message, or push notification. For instance, an interactive sequence can be presented to the patient to allow them to reschedule immediately. This can provide convenience for both the patients and the front office. Specifically, in some examples, one or more alternative empty appointment time slots can be offered to the patient and the patient can select one. Once the patient is notified according to the process described (or if no delay is found), the process ends.

In the present example, although both a location and time are logged when the physician ends the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing.

In some embodiments, multiple processes described with regard to FIGS. 4A-4C can be used to provide feedback to the physician about schedule efficiencies or inefficiencies. For instance, data can be gathered and statistics can be generated for a particular day showing how many appointments were delayed, by how much, and whether the delays were caused by medical assistant delay, physician delay, or appointments that ran longer than the allotted time for the type of exam that was performed. In addition, statistics can be provided over periods of times, from days to months to years, depending on the time specified. In some examples, graphs and/or charts can be provided that show trends. Furthermore, suggestions can be provided based on the data provided, such as whether actual examination times are exceeding the allotted times, and by how much. Percentages can be provided showing how much overrun is occurring and how often. Suggestions such as extending the allotted times for examinations or spacing appointments further apart may be provided.

Figure 5:
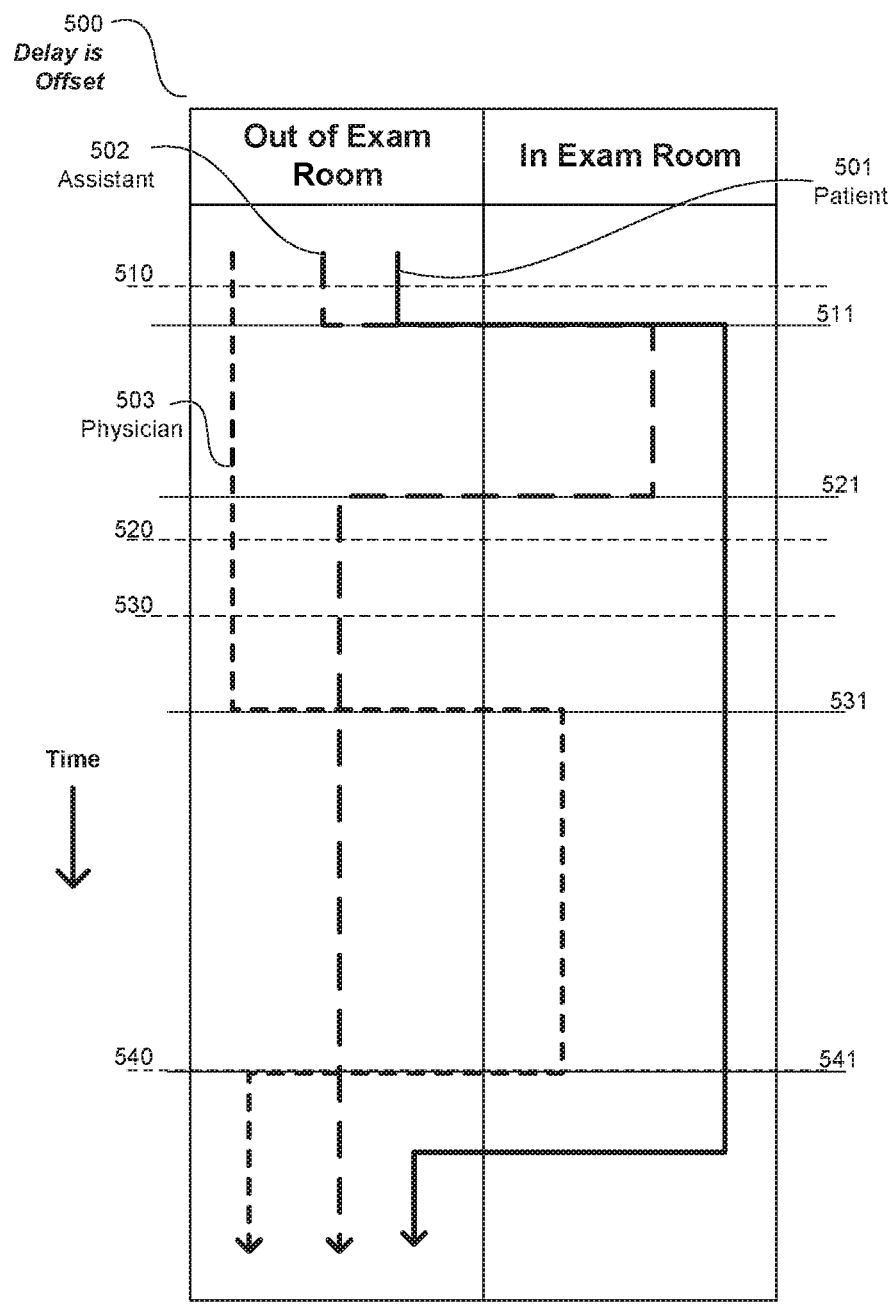
FIG. 5 is a swim-lane diagram of compensated delays of appointments.

With reference to FIG. 5, shown is a swim-lane diagram of compensated delays in appointments. FIG. 3, discussed above, illustrated propagating delays; for successive entries or exits, the delay either remained constant or increased. Delays may not always propagate, however; a delay may be "made up" if a process takes less than the expected time (e.g., a patient arrives with a questionnaire already filled out) or is cancelled altogether (e.g., if a patient "no-shows" or reschedules only a few hours before the appointment). Assistant 502 is scheduled to bring patient 501 to the exam room.at time 510, but does not actually do so until later time 511; the appointment is running behind schedule. After some time taking vital signs and the like, assistant 502 is scheduled to leave the exam room at time 520, but does so at earlier time 521 so that now the appointment is ahead of schedule. Physician 503 is scheduled to enter the exam room at time 530, but does not do so until later time 531, so that the appointment is behind schedule again. However, physician 503 leaves the exam room at time 341, which is equal to scheduled time 540, putting the appointment back on schedule.

The following appointment (and, barring further delays, the appointments following it) may actually start on time. Meanwhile, though, a delay message may have been transmitted at time 511 (or possibly not if this small delay was sub-threshold. Depending on the embodiment, a "back-on-schedule" notification might have been transmitted at time 521, or the system may be programmed to ignore on-schedule events. Another delay message may have been transmitted at time 531 (a longer delay likely to exceed the threshold) and perhaps one or more patients decided to reschedule, but at time 541 there was no longer a delay, therefore no actual need to incur the added overhead of the rescheduling.

Identification of gating events can smooth out such fluctuations in expected delays. After leaving the exam room at time 541, physician 503 is now free to see another patient (or will be after an allotted time to "wrap up" the current appointment). Thus the physician's exit from the exam room at time 541 may be the "gating event" that determines the end of the appointment, making it possible to estimate the beginning of the next appointment. Therefore, in some embodiments the system may log all entries and exits, with or without comparing the logged time with the scheduled time, but it may refrain from transmitting delay messages except when a gating event occurs.

Figure 6:
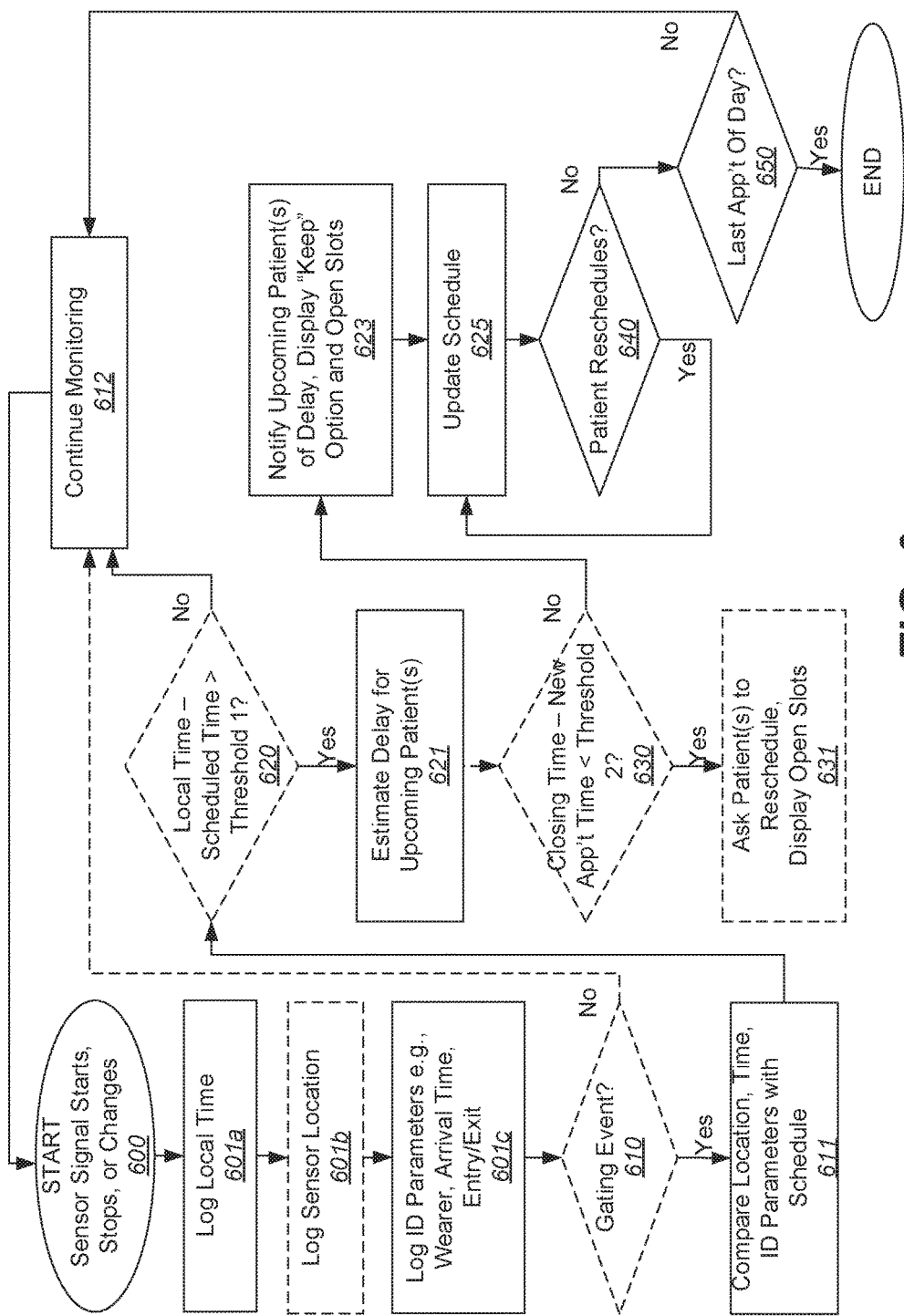
FIG. 6 is a flow sequence illustrating another example of a process for estimating delays for a medical appointment.

With reference to FIG. 6, shown is a flow diagram of an operation that may be implemented as software. Operation 600 may include detecting a position or motion of a first identifier within a sensor range, wherein the sensor range at least partially covers a first service location. A change in the sensor signal, which may include being turned on or off, triggers operations 601a-c, which may include logging a local time 601a, optionally logging a sensor location 601b (e.g., if there are multiple sensors to distinguish or the sensor moves from one service location to another), and logging a first identifying parameter 601c of the first identifier (to identify the particular wearer) in response to an entry of the first identifier into the sensor range or an exit of the first identifier out of the sensor range.

Optional decision 610 may include determining whether the logged entry or exit is a gating event. If so, or if the gating-event determination is omitted, operation 611 may include retrieving a scheduled time of the entry or the exit during a first appointment and subtracting the first scheduled time from the local time to estimate a first delay.

Optional decision 620 may include comparing the first delay to a threshold. If the first delay is greater than the threshold, operation 621 may include estimating the delay of upcoming patients' appointments by adding the first delay to the second scheduled time to compute the expected time of the delayed appointment. Operation 623 may include notifying a first device that the second appointment will be delayed until the expected time and optionally display a selectable "keep" option and a selectable list of open appointment slots on the first device after the notifying. The device may be an employee device, an upcoming patient's device, or both. Selection may be done by typing, touching, clicking, voice, or any other suitable way to choose from a set of options using the device.

Optional decision 630 may calculate whether the delayed time of the day's last appointment has become so late that the office will close before the appointment is completed. If so, the holder of that appointment may be offered rescheduling options but no "keep" option in operation 631. Operation 625 updates the stored schedule for the rest of the day to account for the currently expected delay. The system may respond to an upcoming patient's selection of a "keep" option by replacing the patient's current scheduled time with the expected time of the delayed appointment.

Decision 640 determines whether an upcoming patient has rescheduled and, if so, executes an updating operation 625 replacing the patient's currently scheduled appointment with the rescheduled appointment. In some embodiments, this step may be executed any time any patient requests a reschedule, rather than only in response to a delay notification. Finally, decision 650 determines whether the last appointment of the day has been finished; if not, operation 612 returns the system to monitoring the sensor(s) whenever there is no reason for a delay notification, such as when the most recent event was not a gating event per decision 610 or was not an above-threshold delay per decision 620. If it is determined to be the last appointment at decision 650, the system responds by stopping the process, ceasing to monitor the sensor(s)

FIGS. 7A-7C illustrate examples of delay notifications displayed on device screens. Non-display notifications such as voice-mails are also within the scope of some embodiments.

With reference to FIG. 7A, shown is a cell phone displaying a text message. Most cell phones 701 are able to display a text message 703, which may include details 705 of open appointment slots for rescheduling and enable the user to communicate a choice using the keypad.

With reference to FIG. 7B, shown is a smartphone displaying a push notification from an installed application ("app"). A smartphone 711 may also receive voicemail and text messages, but may include the additional possibilities of push notifications 713 or dedicated apps with graphic user interfaces (GUIs). A GUI may display "Keep" option 715 and open slots 717 as buttons or other clickable or touchable features.

With reference to FIG. 7C, shown is a desktop computer displaying an alert. As well as upcoming patients, employees of the medical office can also benefit from delay notifications by organizing their tasks and breaks around the times when the appointments are likely to begin and end, rather than when the appointments were originally intended to begin and end.

Figure 8:
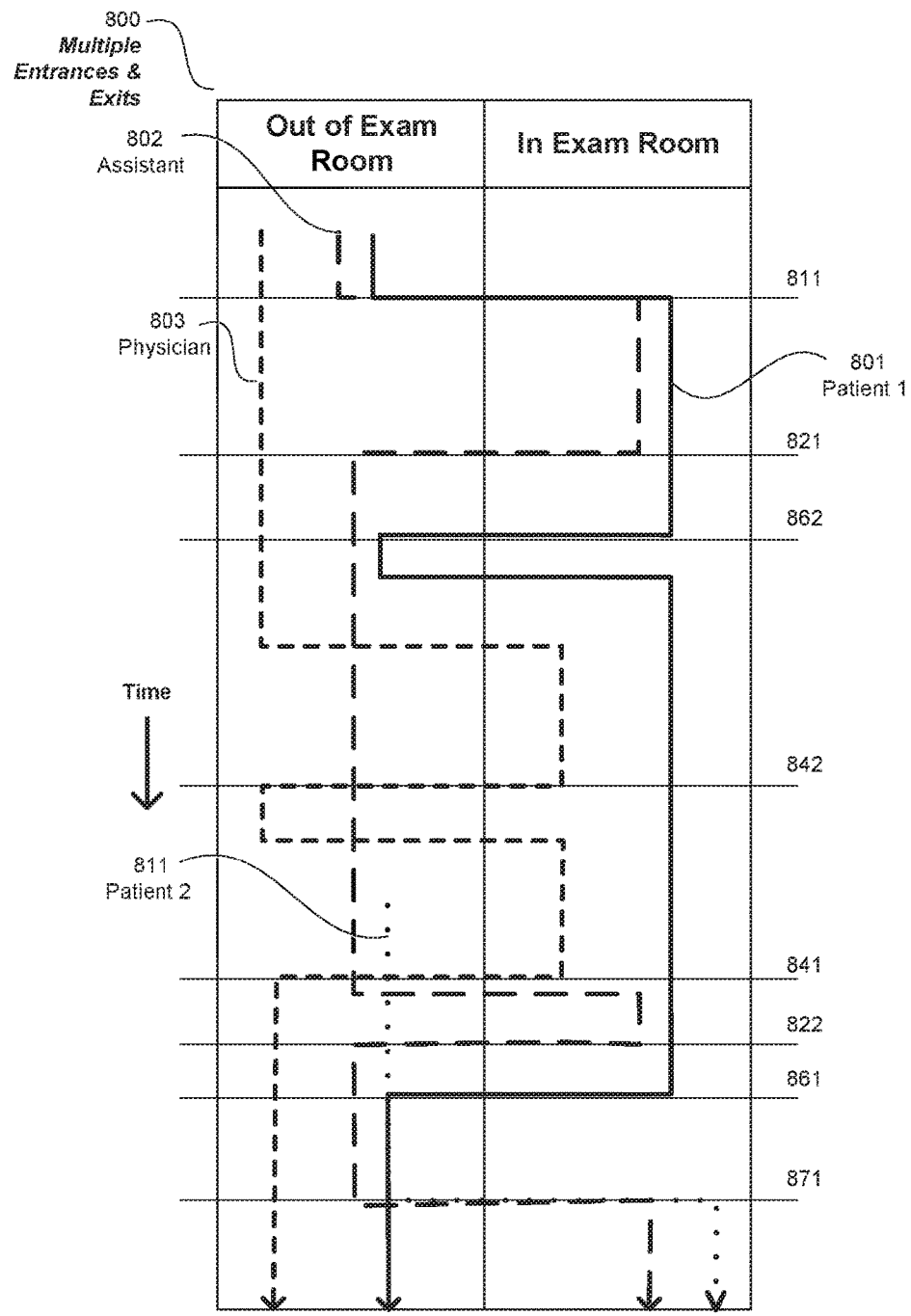
FIG. 8 is a swim-lane diagram of multiple entries and exits of the same individuals to and from an examination room in the course of a single appointment.

With reference to FIG. 8, shown is a swim-lane diagram of multiple entries and exits of participants in a single appointment. Previously it was proposed that the physician's exit from the exam room might be the best indicator of the appointment being over, and therefore a good choice of a gating event. However, if the physician exits the exam room more than once during a single appointment, only the last such exit is preferably used to calculate the delay.

For example, physician 803 exits the exam room at time 842, but only temporarily. Physician 803 may need to answer an urgent question, fetch an injectable, or the like. Shortly thereafter, physician 803 re-enters the exam room, finishes his or her part of the appointment, and re-exits at time 841. Meanwhile, the sensor detects exit 842 and may compute and communicate a delay based on exit time 842. Upon detecting the second exit 841, the system may compare the local time with the NEXT scheduled physician-exit time during the following appointment, which will yield an inaccurate result.

Likewise, assistant 802 may enter the exam room at time 811, collect preliminary information for the physician, and leave at time 821, then enter again to answer logistics questions for an upcoming procedure after the physician exits, and exit again at time 822. If this happens in some types of appointments but not in others, some systems might choose the wrong scheduled time to compare to the second exit.

Patient 801's exit from the exam room might be a better choice of gating item; the sensor would detect patient 801's exit at time 861, then retrieve the log entry for the immediately preceding physician 803 exit at time 841 and calculate the delay from it. In this process, the patient's exit is a "confirming event" signaling that the appointment is over and the physician's most recent exit is therefore the gating event. However, even patient 801 does not necessarily stay in the exam room for the entire appointment. For example, the patient may exit at time 862 to give a sample or answer an administrative question, and then return to the appointment.

Looking further ahead, patient 801's appointment must definitely be over when the next patient 811 enters the exam room at time 871. Therefore, a system can avoid being "confused" by multiple entries and exits of participants in a single appointment by using the entry of the next patient as a confirming event, retrieving the most recent physician exit before time 871, and using it to calculate the delay. This prevents patient 811 from getting updates on delays generated during patient 801's appointment. However, because those updates would likely have been excessively short notice for patient 811 to change plans, the impact is minimal.

Figure 9:
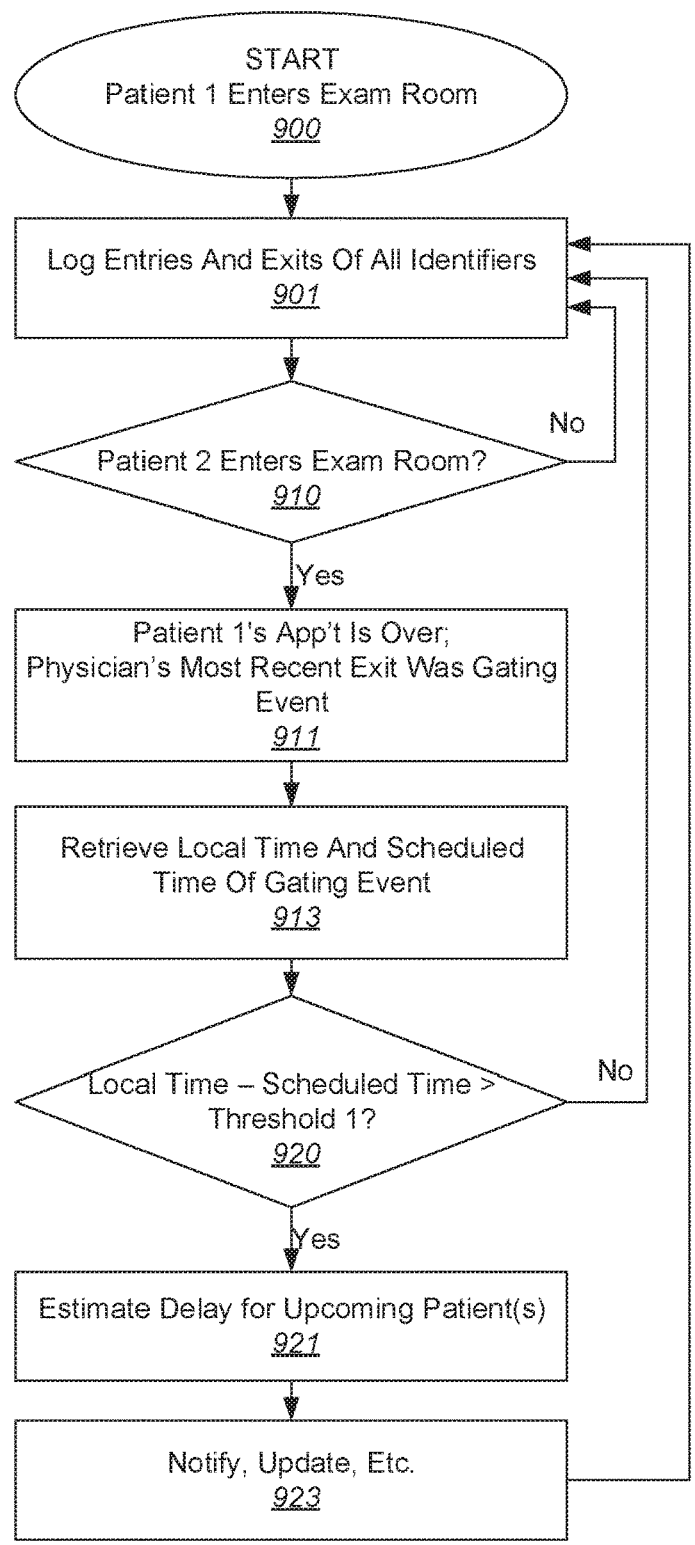
FIG. 9 is a flow sequence illustrating another example of a process for estimating delays for a medical appointment.

With reference to FIG. 9, shown is a flow diagram of a process accommodating multiple entries and exits. An appointment begins with operation 900 with a first patient entering the exam room. Operation 901 may include logging entries and exits detected by the sensor.

After each logging operation, the system decides at decision 910 whether the most recent event confirms that the first patient's appointment has ended. In this example, the confirming event is the entry of a second patient into the exam room. If not, the system may return to operation 910 of monitoring and logging, rather than performing delay calculations. If so, operation 911 may include identifying the most recent event as a confirming event, therefore the last previous physician exit was the gating event. Operation 913 may include retrieving the local time and the scheduled time of the gating event.

Decision 920 determines whether the difference between the gating event's local time and its corresponding scheduled time is greater than a stored threshold. If not, the system may return to operation 910 of monitoring and logging, rather than performing delay calculations. If so, operation 921 may include estimating a delay for upcoming appointments, followed by operation 923 of notifying devices, offering reschedule options, and updating the schedule.

FIGS. 10A-10C illustrate an embodiment in which a patient carries a sensor and the service locations, physicians, and assistants carry active beacons. This type of system tracks the service locations that a patient visits—helpful in practices where patients spend time in treatment rooms, sample collection rooms, the physician's office or conference room, or elsewhere besides an exam room. The system also tracks the time that physicians and assistants spend in proximity to the patient, which may be helpful in settings where patients are examined, tested, or treated in cubicles or bays or at counters that are small and close together with partial dividing walls or none at all.

With reference to FIG. 10A, shown is an example of a medical office floor plan. Optionally, when patient 1001 checks in at reception 1010, office staff member 1006 may use machine 1016 to program an identifying parameter into sensor 1013 that is unique to the patient or the appointment. Sensor 1013 has a sensor range 1043 which in some embodiments may be only 1-2m (3-6') and a built-in clock 1015 or access to some other clock signal.

Assistant 1002 wears beacon 1021 emitting signal 1026, which is detected by sensor 1013 when assistant 1002 escorts patient 1001 to exam room 1020. In some embodiments, signal 1026 may include an identification parameter associates with the assistant wearing it. When patient 1001 enters exam room 1020, sensor 1013 detects exam-room beacon signal 1024 from exam-room location beacon 1022. Signal 1024 may also include an exam-room identification parameter. When assistant 1002 exits the exam room, sensor 1013 stops detecting signal 1026 but continues detecting signal 1024 because patient 1001 is still in exam room 1020.

Meanwhile, physician 1003 in office 1030 wears physician's beacon 1031 transmitting physician's beacon signal 1033 while office location beacon 1023 transmits office beacon signal 1034. When physician 1003 enters exam room 1020, sensor 1013 will begin to detect physician's beacon signal 1033. If physician 1003 then escorts patient 1001 into office 1030 for a conference, sensor 1013 will stop detecting exam-room beacon signal 1024 and begin detecting office beacon signal 1034.

In some embodiments, patient 1001 may return sensor 1013 to member of office staff 1006 when the appointment ends. The timing information logged by sensor 1013 may be uploaded to storage via machine 1016 or some other device. Note that this approach may obviate the need for gating-even and confirming-event capture and the accompanying calculations; when the patient returns sensor 1013, the appointment may be over by definition. Optionally, delay data over a span of time such as a week or a month may be analyzed to diagnose any frequent causes of delay.

With reference to FIG. 10B, shown is a display interface 1051 for programming a patient sensor at the beginning of an appointment. The patient's record number, name, and/or appointment time may be used to identify the log entries uploaded later. The patient arrival time may help derive how many and what lengths of delays are generated when patients arrive late.

With reference to FIG. 10C, shown is a display interface 1052 for uploading data on patient entry and exit times a patient sensor at the beginning of an appointment. Any or all of identifying parameters 1054 may be used to label the data in a database.

Figure 11:
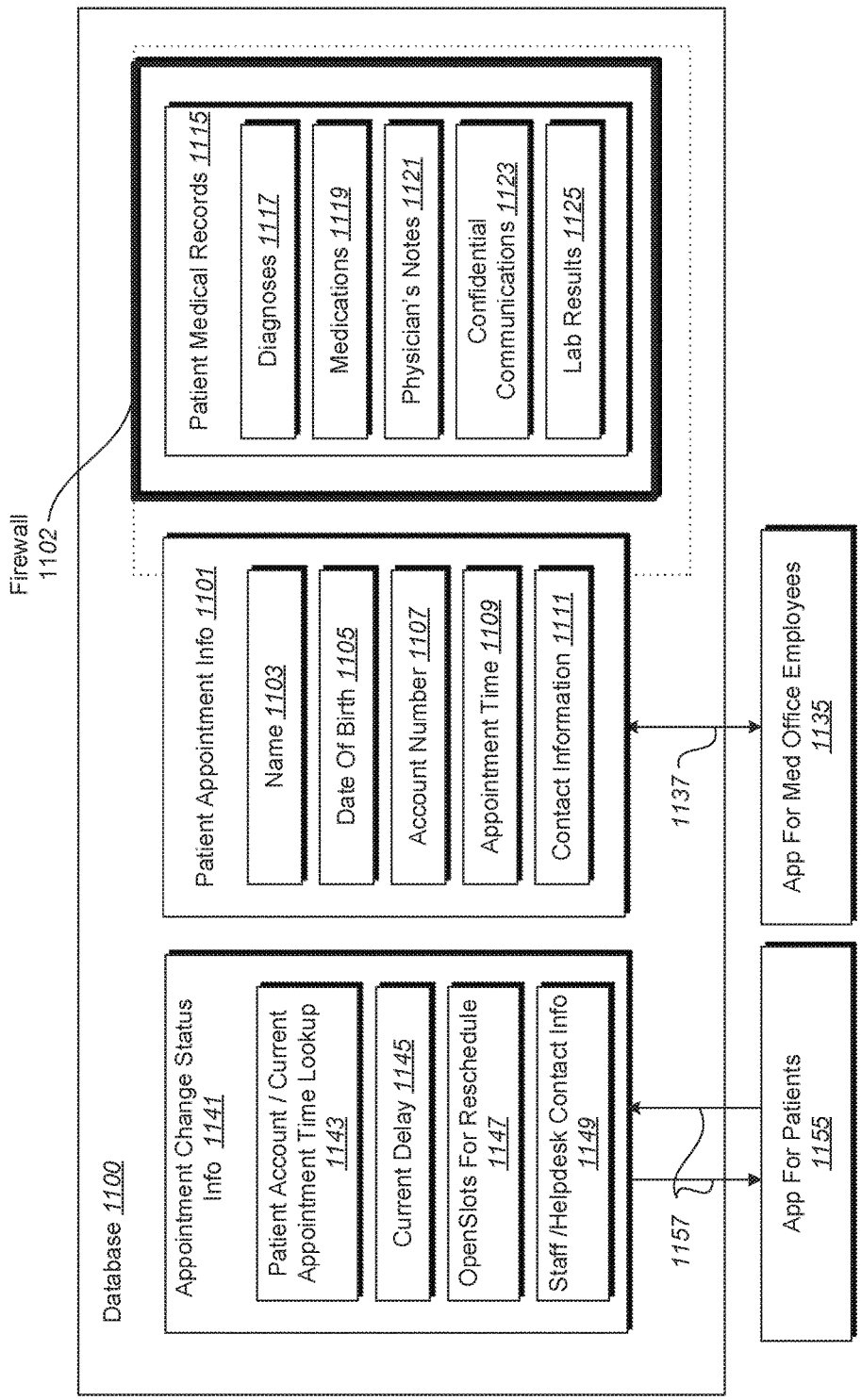
FIG. 11 is a diagrammatic representation of one example of a database designed to store patient information.

With reference to FIG. 11, shown is a diagrammatic representation of one example of a database designed to store patient information. As described above with regard to FIGS. 4A-4C, contact information for patients is retrieved by the notification system when upcoming patients are to be notified of a delay in their appointment times. However, in order to avoid any privacy concerns regarding HIPAA, the notification system is limited to retrieving contact information that is not related to patient-sensitive information.

In the present embodiment, database 1100 includes patient appointment information 1101 and patient medical records 1115. Patient appointment information 1101 includes information for numerous patients such as name 1103, date of birth 1105, account number 1107, appointment time(s) 1109, and contact information 1111. The contact information 1111 can include information such as phone number(s) (for text and/or voicemail), email address, mailing address, and residence address. Additional or different information can be included, depending on the intended use of the database. However, patient appointment information is intended to include information that can be accessed by a scheduling or front office, without concerns about privacy under HIPAA. For example, patient appointment information 1101 may be accessed by an app 1135 on office-employee devices over a network 1137.

In some embodiments, appointment change status information 1141 may be stored in the non-HIPAA portion of the same database 1100. Appointment change status information 1141 may include, without limitation, lookup table 1143 of the latest appointment times held by each patient; current delay information 1145 collected by sensors; available open slots 1147 for patients who opt to reschedule their appointments; and staff and/or helpdesk contact info 1149 for patients who need help with appointment schedule issues. Appointment change status information 1141 may be accessed by an app 1155 on patients' devices over a network 1157, which may or may not be the same as network 1137. In some embodiments, patients' option choices (e.g., to keep a delayed appointment or to reschedule) are received in database 1100 over network 1157.

In the present example, patient medical records 1115 are protected by a firewall 1102 that prevents inadvertent or unauthorized access to patient information protected under HIPAA. The patient medical records 1115 include information for numerous patients such as diagnoses 1117, medications 1119, physician's notes 1121, confidential communications 1123, and lab results 1125. Additional or different information can be included depending on the preferences of the physician or practice. The patient medical records 1115 may include sensitive information that is protected under HIPAA privacy laws. Accordingly, this information must be handled carefully and access to it must be restricted to authorized people and systems.

According to various embodiments described herein, a medical scheduling management system notifies upcoming patients of a delay in their appointment times by accessing patient appointment information such as name 1103, appointment time 1109, and contact information 1111. In some examples, the notification system is implemented as an app for mobile devices. This app 1135 retrieves 1137 patient appointment information to predict schedule delays, such as by retrieving appointment times 1109 and comparing these appointment times 1109 to real-time appointment progress for a particular physician. In addition, this app 1135 retrieves contact information 1111 and names 1103 for patients that are to be notified of upcoming schedule delays. As indicated in the figure, the app 1135 does not have access to patient medical records 1115, and is prevented from accessing these patient medical records 1115 by firewall 1102. Although this example is described in the context of an app that can be implemented on one or more smartphones, mobile devices, etc., it should be recognized that this notification system can be implemented over any computer system. For instance, an office-based computer system can be updated manually by a medical assistant or other personnel to reflect current appointment times and the system can operate without any mobile devices.

Figure 12:
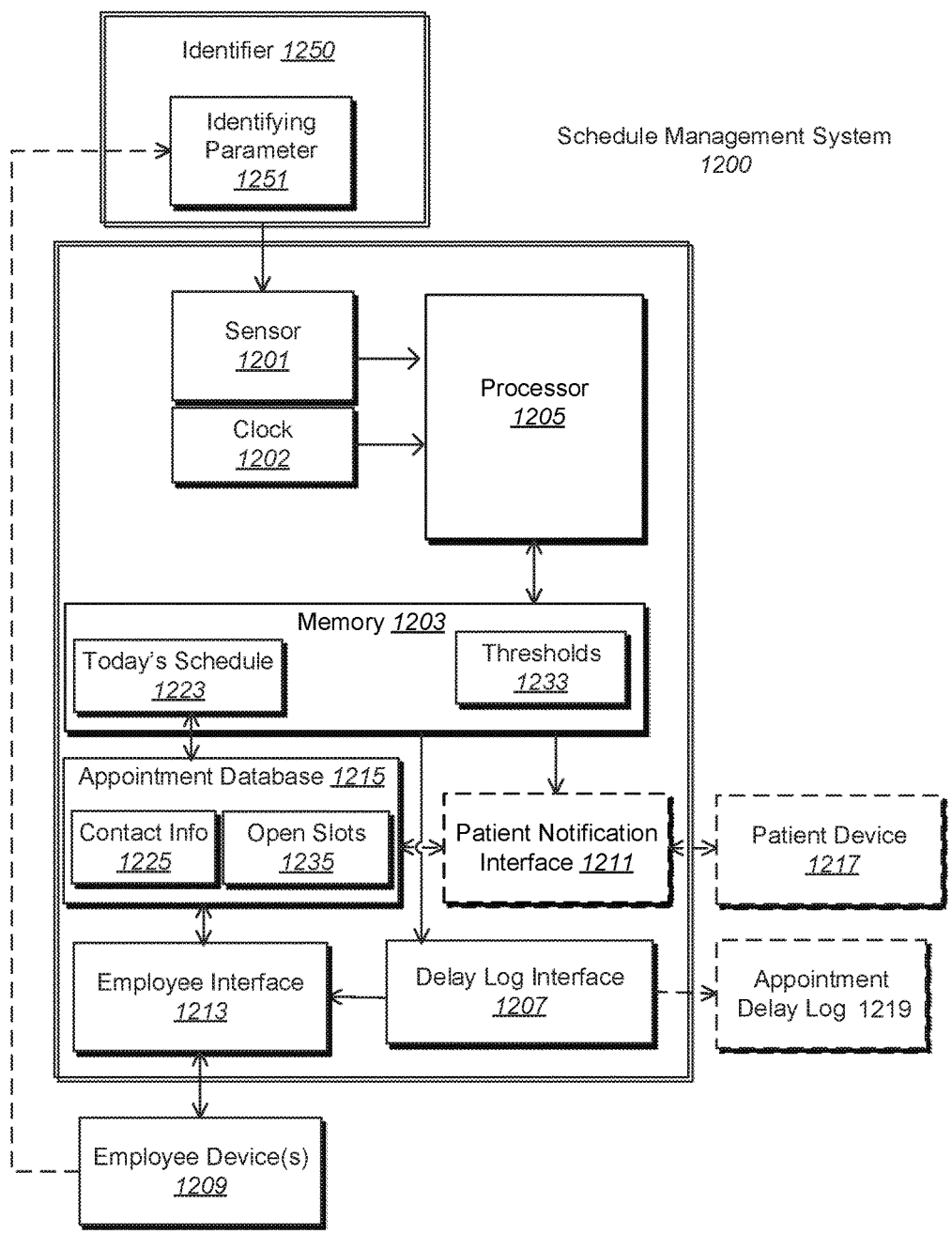
FIG. 12 is a diagrammatic representation of one example of a medical scheduling management system.
Figure 13:
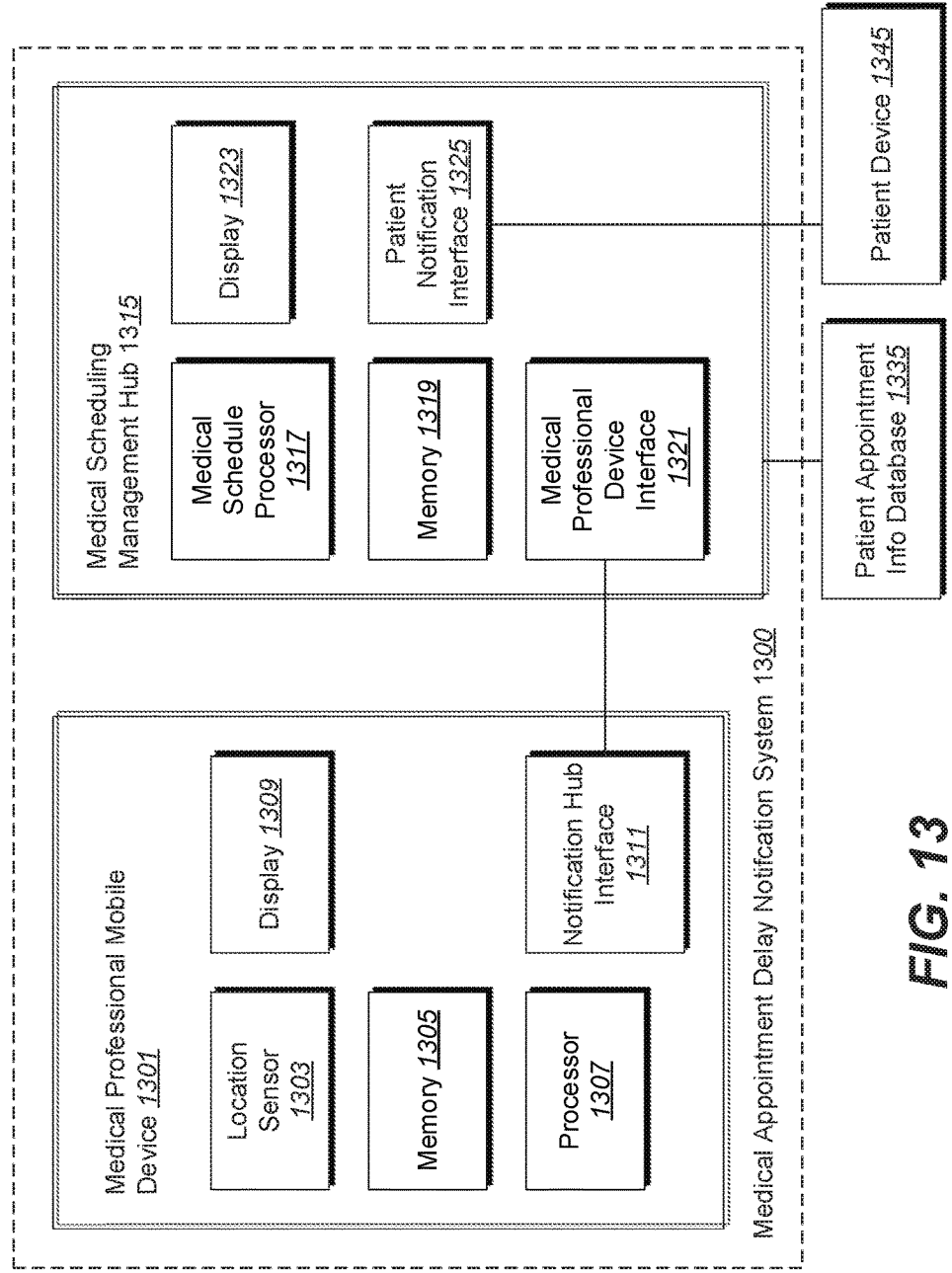
FIG. 13 is a diagrammatic representation of another example of a medical scheduling management system.

As described in previous examples, a medical scheduling management system can be used to predict delays for upcoming appointments and notify upcoming patients of these delays. The medical scheduling management system can be implemented in various ways. FIGS. 12 and 13 illustrate two examples of configurations for medical scheduling management systems. It should be noted that although two particular examples are described, modifications and adjustments can be made within the scope of this disclosure.

With reference to FIG. 12, shown is a diagrammatic representation of one example of a medical scheduling management system. The medical scheduling management system 1200 shown includes identifier 1250, location sensor 1201, clock 1202, memory 1203, medical schedule processor 1205, delay log interface 1207, employee interface 1213, employee device(s) 1209, and patient notification interface 1211. The location sensor 1201 is designed to detect when a medical professional enters an examination room to conduct an examination of a particular patient. Clock 1202 tracks the local time that is captured by processor 1205 when sensor 1202 detects the appearance or disappearance of an identifier. This location sensor 1201 can be implemented in numerous ways. In one example, a medical professional wears an identifier 1250 that is detectable in different areas of the office. The system is able to detect when identifier 1250, such as an RFID, etc. is in proximity to the location sensor. In some applications, there may be multiple identifiers simultaneously detected by a sensor. The processor, by extracting identifying parameter 1251, can discern whose identifier was detected by sensor 1201. In some applications, there may be multiple location sensors in the system.

In other examples, the location sensor 1201 represents an input interface used by a medical assistant or other personnel to enter the location of the medical professional at a particular time. Specifically, location and time information can be entered manually into the system. In some instances, the location sensor 1201 represents an input interface used by the medical professional to indicate when a particular appointment has started. Specifically, location and time information can be entered manually into the system. For instance, the next scheduled appointment may pop up or be otherwise selectable on a mobile device, and when the medical professional selects a button, the time is logged and this time is compared with the scheduled time. In yet other embodiments, the medical scheduling management system 1200 can be implemented as an app on a mobile device, such as a smartphone. In these examples, the location sensor 1201 can implement technologies such as GPS or other location sensing systems. In some examples, the location sensor 1201 can be omitted, such as when only the patients and times are logged.

In the present embodiment, the medical schedule processor 1205 is designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule may not include any HIPAA information. The memory 1203 is used to store data, which may include the present day's schedule 1223 and stored thresholds 1233, store program instructions, and maintain a local side cache. The program instructions may control the operation of an operating system and/or one or more applications, for example. In addition, display 1209 is used to allow a user to interact with the system, such as through a monitor, screen, etc.

In the present embodiment, the notification interface 1211 is used to notify upcoming patients if their appointments will be substantially delayed, as described in more detail with regard to FIGS. 4A-4C above. This notification interface 1211 is also designed to notify upcoming patients if their appointments need to be rescheduled. In some examples, the notification interface 1211 is also designed to provide an option for these patients to reschedule their appointments. As described above, the notification interface 1211 contacts a patient device 1217 using patient contact information such as a phone number, email, etc. In some examples, the notification interface 1211 notifies a patient via a text message. In other examples, the notification interface 1211 notifies a patient via a voicemail or email. Other notification modes can also be used, depending on the preferences of the patient and medical office.

In the present example, delay log interface 1207 allows data such as real-time location and time information for appointments in-progress to be transmitted to an appointment delay log 1219. This appointment delay log 1219 is located in a separate location that may be accessed by other devices. For instance, if the medical scheduling management system 1200 is implemented as an app on a mobile device, the appointment delay log 1219 may include an office computer that is accessible to office staff and personnel. In other examples, the appointment delay log 1219 can be located on a cloud drive. However, the delay log interface 1207 and appointment delay log 1219 can be omitted in some applications, depending on the needs of the practice.

As shown in the present embodiment, the medical scheduling management system 1200 can interact with a patient appointment information database 1215, such as the one shown and described with regard to FIG. 11. Patient appointment information database 1215 may include patient contact information 1225 and open appointment slots 1235. In particular, the medical scheduling management system 1200 accesses the patient appointment information database 1215 when predicting delays, when notifying upcoming patients by messaging their devices such as patient device 1217, and when notifying medical-office employees through employee interface 1213 via employee devices 1209. As mentioned with regard to FIG. 11, the information accessible in the patient appointment information database 1215 is not data that is protected under HIPAA.

With reference to FIG. 13, shown is a diagrammatic representation of another example of a medical scheduling management system. In this example, the medical scheduling management system 1300 includes a medical scheduling management hub 1315 and one or more medical professional mobile devices 1301. The medical professional mobile device 1301 can be implemented as a mobile device, such as a smart phone, tablet, etc. In other examples, this mobile device 1301 can be implemented as a wearable device such as a bracelet, fob, charm, clip, etc. In some embodiments, the medical professional mobile device 1301 is a specialized device with added security and firewall capabilities to separate information that is protected under HIPAA, further described with reference to FIG. 11.

As shown, the medical scheduling management hub 1315 is implemented on a computer such as a mobile device, office computer, server, etc. This serves as a "home base" for the system. In some examples, this hub 1315 is implemented on a central office computer or on the cloud. In the present example, the medical professional mobile device 1301 includes a location sensor 1303, memory 1305, processor 1307, display 1309, and notification hub interface 1311. The location sensor 1303 is designed to detect when a medical professional enters an examination room to conduct an examination of a particular patient. This location sensor 1303 can be implemented in numerous ways. In one example, the location sensor is able to identify when the medical professional is in different areas of the office. In these examples, the location sensor 1303 can implement technologies such as GPS, RFID, Bluetooth, triangulation mechanisms, cameras, or other location sensing systems. In other examples, the location sensor 1303 represents an input interface used by the medical professional to indicate when a particular appointment has started. Specifically, location and time information can be entered manually into the system. For instance, the next scheduled appointment may pop up or be otherwise selectable the mobile device 1301, and when the medical professional selects a button, the time is logged and this time is compared with the scheduled time. In some embodiments, the location sensor 1303 can be omitted, such as when only patient and time information are logged.

In the present example, the medical professional mobile device 1301 includes memory 1305, which is used to store data and program instructions and maintain a local side cache. The program instructions may control the operation of an operating system and/or one or more applications, for example. In some examples, the size of the memory 1305 may be limited, as when most of the processing and storage of data is performed at the medical scheduling management hub 1315. In addition, the processor 1307 may include limited processing of the data collected. For instance, the data collected may include the times and locations of particular appointments, and the processor can be used to format the information before sending it to the medical scheduling management hub 1315. The limited memory 1305 and processor 1307 sizes and capabilities may be appropriate especially in cases when the medical professional mobile device 1301 is implemented as a wearable because the components can be smaller and more conveniently designed into a smaller casing to be comfortably worn. In the present example, display 1309 is used to allow the medical professional to interact with the system, such as through a screen, touch screen, etc. As described above, the medical professional may input data through this display 1309 and/or view options through the display.

In the present example, the medical professional mobile device 1301 also includes a notification hub interface 1311. This notification hub interface 1311 is used to communicate with the medical scheduling management hub 1315. In particular, data regarding real-time appointment start times are sent via the notification hub interface 1311 to the medical scheduling management hub 1315 via medical professional device interface 1321. In some examples, the medical professional device interface 1321 is used to send messages to the medical professional mobile device 1301 via the notification hub interface 1311, such as "Has the Smith 1:10 pm appointment begun?"

In the present embodiment, the medical scheduling management hub includes a medical schedule processor 1317 designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule does not include any HIPAA information. The memory 1319 is used to store data and program instructions and maintain a local side cache. The program instructions may control the operation of an operating system and/or one or more applications, for example. In addition, display 1323 is used to allow a user to interact with the system, such as through a monitor, screen, etc.

In the present embodiment, the patient notification interface 1325 is used to notify upcoming patients if their appointments will be substantially delayed, as described in more detail with regard to FIGS. 4A-4C above. This notification interface 1325 is also designed to notify upcoming patients if their appointments need to be rescheduled. In some examples, the notification interface 1325 is also designed to provide an option for these patients to reschedule their appointments. As described above, the notification interface 1325 contacts a patient 1345 using patient contact information such as a phone number, email, etc. In some examples, the notification interface 1325 notifies a patient via a text message. In other examples, the notification interface 1325 notifies a patient via a voicemail or email. Other notification modes can also be used, depending on the preferences of the patient and medical office.

As shown in the present embodiment, the medical scheduling management hub 1315 interacts with a patient appointment information database 1335, such as the one shown and described with regard to FIG. 11. In particular, the medical scheduling management hub 1315 accesses the patient appointment information database 1335 when predicting delays and when notifying upcoming patients, such as patient 1345. As mentioned with regard to FIG. 11, the information accessible in the patient appointment information database 1335 is not data that is protected under HIPAA.

Although FIGS. 12 and 13 describe particular configurations of medical scheduling management systems, it should be recognized that various configurations can be constructed within the scope of this disclosure. In addition, the system can be used to provide feedback to the physician and/or practice to allow them to generate physician/examination efficiency reports in some examples. For instance, the system can generate reports indicating the percentage of appointments that were delayed and by how much they were delayed. In some cases, the reports can be customizable to indicate factors such as whether certain types of appointments are delayed more often, times of day when more appointments are delayed, days of the week or month when appointments are delayed more often, etc. This feedback can be used by the physician to improve their care and service and become more efficient in their practice. This can lead to more satisfied patients, a more pleasant experience for the patients and medical professionals, and a higher rate of return for the physician and practice.

These and other configurations of medical scheduling management systems are further described in U.S. patent application Ser. No. 14/794,851 titled MEDICAL SCHEDULING MANAGEMENT SYSTEM by Bullington et al., filed on Jul. 9, 2015; and U.S. patent application Ser. No. 14/794,852 titled PHYSICIAN EFFICIENCY ANALYSIS SYSTEM by Bullington et al., filed on Jul. 9, 2015; and U.S. patent application Ser. No. 14/794,854 titled VIRTUAL WAITING ROOM FOR MEDICAL APPOINTMENTS by Bullington et al., filed on Jul. 9, 2015; and U.S. patent application Ser. No. 14/794,857 titled MEDICAL APPOINTMENT PROGRESS TRACKING by Bullington et al., filed on Jul. 9, 2015; and U.S. patent application Ser. No. 15/333,087 titled APPOINTMENT SCHEDULING MANAGEMENT SYSTEM by Bullington et al., filed on Oct. 24, 2016. The above mentioned applications are incorporated by reference herein in their entirety and for all purposes.

In various embodiments, one or more components of a medical scheduling management system, such as medical scheduling management system 1200, may be located within a single apparatus, such as sensor module 205. In some embodiments, a sensor module 205 may comprise a lighting device, such as a light bulb.

Figure 14:
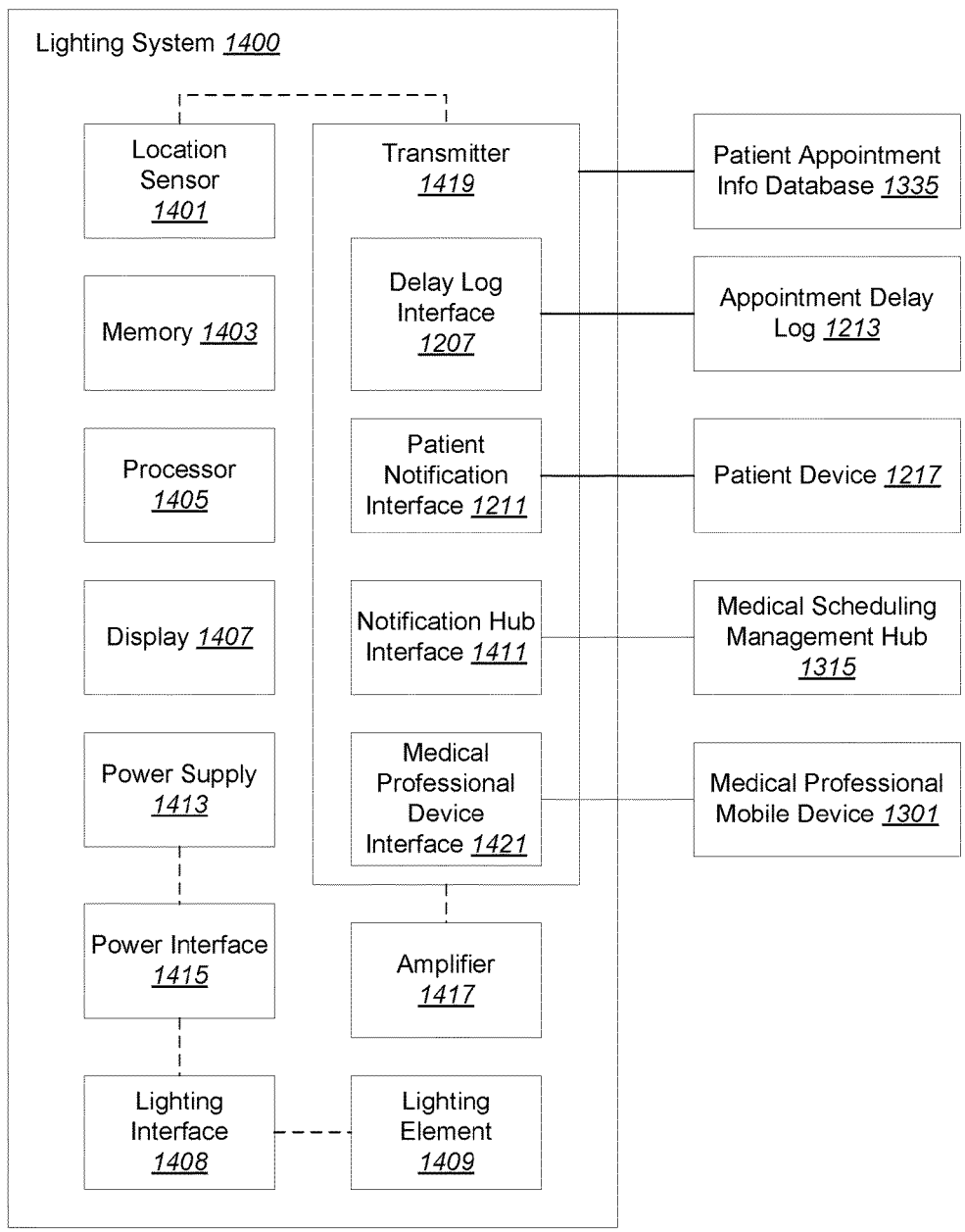
FIG. 14 is a diagrammatic representation of an example of a lighting system for medical scheduling management, in accordance with one or more embodiments.

With reference to FIG. 14, shown is a diagrammatic representation of an example of a lighting system for medical scheduling management, in accordance with one or more embodiments. In some embodiments, lighting system 1400 may be a light bulb that can be used in any room with an appropriate terminal. In some embodiments, lighting system 1400 may comprise lighting element 1413. In some embodiments, lighting element 1413 may be a component of lighting system 1400 which emits light for lighting a room, such as an examination room. For example, lighting element 1413 may be a metal filament, such as tungsten, which is housed in a sealed, oxygen-free chamber. In another example, lighting element 1413 may be a light emitting diode (LED) lighting system.

In some embodiments, lighting system 1400 may comprise a light fixture and lighting element 1413 may be a light bulb that is used within lighting system 1400. In some embodiments, lighting element 1413 may be an incandescent lamp with a wire filament. In further embodiments, lighting element 1413 may comprise a light emitting diode (LED) lamp including one or more LED chips. In yet further embodiments, lighting element 1413 may comprise a compact fluorescent lamp (CFL).

In various embodiments, lighting element 1413 may be connected to lighting system 1400 via a lighting interface 1408. For example, where lighting system 1400 comprises a light bulb, such as an incandescent light bulb, the lighting interface 1408 may comprise a base. Such base may be configured to couple to a power source via one of various standard E27 screw, or other Edison screw coupling. The base may further be configured with a bottom terminal contact for transferring electrical power to a fuse lead-in to heat the filament lighting element 1413. As another example, where lighting system 1400 comprises an LED lighting system, lighting interface 1408 may comprise an anode lead and a cathode lead, which couple to a power source to provide electrical current to the light emitting diode lighting element 1413.

In embodiments, where lighting element 1413 comprises a light bulb, lighting system 1400 may be configured to attach to a power source of the exam room at an electrical terminal. In other embodiments, lighting system 1400 may be electrically connected to the power source of the exam room. Such lighting system may include a lighting interface 1408 comprising one or more different couplings for lighting element 1413, such as a standard E27 screw, other Edison screw coupling, etc.

In some embodiments, lighting system 1400 is located at the center of a room, such as a medical examination room. Lighting fixtures are generally positioned in the center of a room. In various medical settings lighting fixtures are centrally positioned to provide optimal lighting for examinations and/or procedures. For example, an examination table and/or chair may be located in the center of an examination room with lighting system 1400 positioned above on the ceiling. Since a lighting structure in a medical examination room may be centered about the location of a patient during an examination and/or procedure, a signal transmitted from and/or received by a lighting system 1400 may correspond more closely to the occurrence of an examination and/or procedure.

Lighting system 1400 may comprise location sensor 1401. In various embodiments, location sensor 1401 is a transceiver which may transmit and/or receive various wireless signals, including Wi-Fi, Bluetooth, etc. In some embodiments, location sensor 1401 may be sensor 213 and/or sensor 1303. As previously described, sensor 1401 may connect to a user device, such as a ID tag or mobile device, including medical professional mobile device 1301, which corresponds to a particular individual, such as a medical professional (including physicians, assistants, etc.) or a patient. This connection may indicate the presence of the corresponding individual within the examination room.

As previously described, sensor 1401 may be configured to detect an ID that may be an active beacon or a non-powered readable tag. For example, sensor 1401 may emit an electromagnetic signal which impinges on an identifier comprising an RFID or infrared tag to power a return signal, as previously described with reference to FIG. 2B. As another example, sensor 1401 may detect a signal emitted from the ID, such as Bluetooth or Wi-Fi signal, as previously described with reference to FIG. 2C. In a further example, a user device may transmit a signal which can be detected by sensor 1401 to form a connection. In various embodiments, sensor 1401 detects a signal to determine whether an individual (patient, assistant, doctor, etc.) is in or out of the exam room, as previously described with respect to FIGS. 2D and/or 2E.

In some embodiments, a centrally located lighting system may allow a wireless signal to have a comprehensive coverage of a particular room. In other embodiments, this may allow for a wireless signal with a range comprising a uniform radius to be emitted without extending beyond the walls of the room. By using a light bulb or lighting system as the source of a sensor and/or transmitter, an omnidirectional wireless signal with a uniform signal range may be used to cover an exam room. For example, in a room with four walls of equal dimensions, a wireless signal with a signal range of equal diameter may be used to cover all or a majority of the room with minimal or not wireless signal extending beyond the walls of the room.

In some embodiments, lighting system 1400 may be configured to emit a wireless signal with a signal range of a desired shape to correspond to the characteristics of a given room. For example, directional wireless transmitters or antenna may be implemented to provide an aggregated signal with a signal range of a particular shape. For example, a room with four walls may be a rectangular configuration with two opposite walls further from each other than the two other opposite walls. In such an example, an omnidirectional wireless signal may be used to reach the two closer walls, while directional transmitters may be used to extend the signal range to reach the two further walls. Thus, a signal that is transmitted from and/or received by lighting system 1400 may be more closely correlated with the presence of a particular individual within the room. In various embodiments, lighting system 1400 may be configured to emit a signal to correspond to various shapes and sizes of rooms.

In some embodiments, the wireless signal transmitted by lighting system 1400 may be tuned to a signal strength corresponding to the size of the corresponding room (such as an exam room or a medical office). In various embodiments, the signal strength may be tuned by adjusting the gain in a signal amplifier, such as amplifier 1417. For example, a lower signal strength may be tuned for a smaller exam room such that the range of the wireless signal is decreased and does not extend beyond the walls of the exam room. As another example, a larger signal strength may be tuned for a larger exam room such that the range of the wireless signal is increased to reach the walls of the exam room. In some embodiments, a predetermined localized signal range around lighting system 1400 may be desired. For example, lighting system 1400 may be positioned at the center of an exam room above an examination area, and may be tuned to include a signal with a localized range of three feet. Thus, any user device may detect the wireless signal when within three feet of the examination area.

In various embodiments, software applications may be implemented to tune the strength. In some embodiments, such software applications may be installed on a computer server, such as medical scheduling management hub 1315, which may communicate tuning instructions to lighting system 1400 via notification hub interface 1411. In some embodiments, such software applications may be installed on various other devices, such as medical professional mobile device 1301, which may communicate tuning instructions to lighting system 1400 via medical professional device interface 1421.

Thus, a centrally located wireless transmitter and/or location sensor may provide a more accurate indicator of when a particular individual is within the room. Through tuning and other directionality functions, a wireless signal may be created that corresponds to the characteristics of a particular room. This may also function to prevent or reduce the occurrence false readings where part of the wireless signal range extends beyond the room (such as when the doctor is in the hallway near the room, but is recorded as being in a room). For example, if a sensor/transmitter is located too close to the entrance of the exam room, part of the wireless signal range may extend beyond the exam room into the hallway.

In particular embodiments, the location of an individual may depend upon the strength of the connection or signal detected between sensor 1401 and a user device. A stronger signal may correspond more closely to the presence of an individual in a room because a signal detected at a transceiver in a first medical office may be several times stronger if a doctor is in the first medical office than if the doctor is in a different medical office. For example, location information of an individual may not be recorded and/or detected until a user device corresponding to that individual detects a signal transmitted by sensor 1401 that is above a predetermined threshold signal strength. In some embodiments, such signal strength may be measured in decibel-milliwatts (dBm). As another example, where the user ID is a non-powered readable tag, the user ID may not be configured to power a return signal until the electromagnetic signal emitted by sensor 1401 impinges on the user ID above a predetermined threshold signal strength. In yet another example, where the user device transmits a wireless signal, location sensor 1401 may only record location information when the detected signal transmitted by the user device is above predetermined threshold signal strength.

Additionally, and/or alternatively, the location of an individual may depend upon the duration of the connection or signal detected between sensor 1401 and a user device. For example, as previously described, sensor 1401 may emit a signal as long as a user device is in range. The location of an individual may be established and recorded when the duration of the connection between sensor 1401 and a user device exceeds a predetermined threshold, such as one minute for example. As also previously described, sensor 1401 may emit a pulse at a regular interval which forms a connection with the user device when in range. A location of an individual may be established and recorded when a predetermined number of signal pulses are detected by the user device, such as 4 pulses for example. In yet another example, a user device may emit a pulse at a regular interval which may be detected by sensor 1401. A location of an individual may be established and recorded when a predetermined number of signal pulses are detected by sensor 1401. In these described examples, as long as a signal is detected at a regular interval, it can be determined that the user device, and the corresponding individual, is within range, and within the room. This may differentiate a more temporary connection made when an individual merely passes by the room in the hallway.

In some embodiments, a localized signal range may be implemented for adjustable lighting systems 1400 that may be moved to desired illumination locations in order to detect the localized presence of a medical professional and/or patient. For example, in some embodiments, the position of lighting system 1400 may be adjustable, in which lighting system 1400 may be moved around an examination area for desired illumination angles of the examination area and/or a patient. Because lighting system 1400 may be adjusted by a medical professional (such as a physician or medical assistant) to illuminate a patient and/or a particular area of the patient, in various examples, the position of lighting system 1400 may closely correspond to the location of such patient, medical professional and/or other individual or user. Thus, the proximity of an individual to lighting system 1400 may indicate when an examination has begun or is in progress. In such an example, location sensor 1401 and/or transmitter 1419 may be tuned to include a signal with a localized range of three feet.

In further embodiments, lighting system 1400 may include transmitter 1419. In some embodiments transmitter 1419 may be transmitter/receiver 216, which functions both to transmit and receive signals. Such transmitter 1419 may be configured to transmit the location status of the individual to a remote processor, such as remote processor 234. For example, transmitter 1419 may include delay log interface 1207, which allows data such as real-time location and time information for appointments in-progress to be transmitted to an appointment delay log 1219, as previously described. Additionally, and/or alternatively, transmitter 1419 may include patient notification interface, which notifies upcoming patients if their appointments will be substantially delayed, such as at a patient mobile device 1217, as previously described.

In some embodiments, transmitter 1419 may be configured to transmit location status to a medical scheduling management hub 1315 via notification hub interface 1411. As previously described with reference to notification hub interface 1311, notification hub interface 1411 may send data regarding real-time appointment start times to the medical scheduling management hub 1315 for processing. In some embodiments, transmitter 1419 may be configured to transmit location status to a medical professional mobile device 1301 via a medical professional device interface 1421. As previously described with reference to medical professional mobile device interface 1321, medical professional mobile device interface 1421 is used to send messages to the medical professional mobile device 1301, such as "Has the Smith 1:10 pm appointment begun?" In some embodiments, transmitter 1419 may be configured to transmit and receive data from patient appointment info database 1335.

In certain embodiments, location sensor 1401 may transmit a wireless signal to a user device, such as medical professional mobile device 1301 or patient device 1217 via transmitter 1419. In some embodiments, transmitter 1419 may be an integral component of location sensor 1401. For example, transmitter 1419 may function as an active beacon that transmits a signal to one or more medical professional mobile devices, such as 1301, previously described with reference to FIG. 13. In various embodiments, transmitter 1419 may transmit a wireless signal, such as Wi-Fi, Bluetooth, etc. For example, each medical professional mobile device may include a location sensor that can detect the signal transmitted by transmitter 1419. More specifically, the transmitter 1419 may transmit a signal to a location sensor 1303. A signal detected by location sensor 1303 in the mobile device 1301, may indicate when a medical professional enters or leaves an examination room. The mobile device may then store such location information on a memory, such as 1305, and may process such data via processor 1307. Alternatively, and/or additionally, the mobile device may transmit the location information to medical scheduling management hub 1315 for processing via notification hub interface 1311.

Various embodiments of lighting system 1400 described herein may provide additional privacy protections within a medical setting. By constraining the signal range to within an examination room, lighting system 1400 may not be accessed by devices outside of the examination room. Thus, lighting system 1400 may not be subject to unauthorized access by devices not within the examination room, reducing the risk of unauthorized access to sensitive medical information, such as medical records 1115.

Lighting system 1400 with an integrated transceiver may provide additional privacy protections for sensitive private medical information. For example, lighting system 1400 may provide an additional separation between the location data and the contact information stored in non-HIPAA portions of a database, as well as the medical records 1115 stored in firewalled HIPAA portions of the database, as described in FIG. 11. For example, location sensor 1401 may be used to detect a unique identification code transmitted by an ID tag corresponding to a patient and/or medical professional. Such unique identification code may be matched with information corresponding to the patient and/or medical professional stored in memory 1403 at lighting system 1400, such as by processor 1405. In some embodiments, such identification code may be matched to corresponding information by a secure server, such as schedule management system 1200 and/or medical scheduling management hub 1315. Thus, there may be an additional separation between the location information of a patient (which may correspond to when an examination is occurring) and the patient appoint info 1101, which is further separated from the patient medical records 1115.

In some embodiments, the unique identification code corresponding to a particular individual may constantly change or cycle through a list of identification codes. Such code changes may be synced at lighting system 1400, such as by processor 1405, so that location tracking can be matched with information corresponding to that individual. In some embodiments, such changes may be synced at a secure server, such as schedule management system 1200 and/or medical scheduling management hub 1315.

In various embodiments, components in lighting element 1413 may function as an antenna to transmit and/or receive signals, such as the radio frequency (RF) signals (shown by the dashed line). In some embodiments, lighting element 1413 may function as an antenna for location sensor 1401 and/or transmitter 1419. For example, a lighting system 1400 acting as an active beacon may transmit a signal through the wire filaments of an incandescent lamp. In another example, the wire filaments of an incandescent lamp in lighting system 1400 may receive a signal transmitted by an ID beacon. In other embodiments, the diode of an LED lamp may also function to transmit and/or receive signals. For example, a high frequency signal may be applied through the DC voltage to be transmitted from the diode along with the light.

Including the sensor/transmitter and/or transceiver in lighting system 1400 allows the medical scheduling management system to be incorporated into an essential structure of the exam room. No additional structure is required. This may eliminate potential clutter in an exam room in which space may already be designated for various tools, furniture, and other essential appliances. Light bulbs and other lighting elements 1409 are also easily interchangeable and are easily replaced or used in any room with a standardized terminal.

In the present example, lighting system 1400 may include memory 1403, which is used to store data and program instructions and maintain a local side cache. The program instructions may control the operation of an operating system and/or one or more applications, for example. In some examples, the size of the memory 1403 may be limited, as when most of the processing and storage of data is performed at the medical professional mobile device 1301 and/or medical scheduling management hub 1315. In addition, processor 1405 may include limited processing of the data collected. For instance, the data collected may include the times and locations of particular appointments and processor 1405 can be used to format the information before sending it to the medical professional mobile device 1301 and/or medical scheduling management hub 1315. The limited memory 1403 and processor 1405 sizes and capabilities may be appropriate especially in cases when lighting system 1400 is implemented as a standard lighting device for an exam room because the components can be smaller and more conveniently designed into a smaller casing to reduce obstruction and remain out of sight.

In various embodiments, lighting system 1400 may include display 1407. In some embodiments, display 1407 may indicate that the location sensor 1401 has detected that an individual is in the exam room. For example, a light may be turned on to indicate that location sensor 1401 has detected the presence of a particular individual. There may be multiple lights, where each light indicates a separate individual with an ID. The lights may be switched off when the corresponding individual leaves the exam room. In other embodiments, display 1407 may indicate various status messages of lighting system 1400, including power status, error messages, etc. In some embodiments, display 1407 may further display the time, temperature, lighting level, etc. In some embodiments, display 1407 includes user input means to allow the medical professional to interact with the system, such as through a screen, touch screen, etc. As described above, the medical professional may input data through this display 1407 and/or view options through the display 1407.

In one or more embodiments, one or more components of lighting system 1400 may be powered by the power source from the corresponding room. For example, a power interface 1415 may be wired into the electrical circuit of the room and/or building, which may in turn be coupled to a greater electrical grid. In this way, the various components of lighting system 1400 depicted in FIG. 14 may have access to continuous power. In some embodiments, functioning of lighting element 1409 may be controlled by a switch or other mechanism. However, location detection components depicted in FIG. 14, (such as sensor 1401, memory 1403, processor 1405, display 1407, transmitter 1419, and/or other components) may alternatively, and/or additionally, receiver power from a separate circuit from lighting element 1409. For example, sensor 1401 may be electrically coupled in parallel. This ensures that electrical power may continue to power the location detection functions even when the light is turned off, which may occur for various examination purposes. For example, the assistant or physician may still be in the exam room when the light is turned off, but it may be determined that the physician has left the exam room if the location detection components were also turned off. In some embodiments, function of lighting element 1409 may be controlled by a separate switch mechanism from the function of various other components of lighting system 1400. Thus, power may be continuously supplied to the components of lighting system 1400, but the circuit for lighting element 1409 may be open and closed via a separate switch mechanism.

In some embodiments, a separate power supply 1413 is included to power one or more components of lighting system 1400. In some embodiments, power supply 1413 is electrically coupled to power interface 1415. In some embodiments, the power supply 1413 may comprise a separate battery included in the lighting system 1400 to power the location detection components. In yet further embodiments, the battery may be a rechargeable battery that is charged by the electrical power source of the exam room. For example, power supply 1413 may be charged by the power source of the room when a switch is activated to power lighting element 1409. In some embodiments, the power supply 1413 comprises a capacitor which may store a charge from the electrical power source. Such capacitor may build up and store a charge when the exam room's power is turned on. In some embodiments, the capacitor may store enough charge to power the location detection components for a predetermined amount of time, such as 12 hours. Complete power loss of the location detection components after 12 hours may be acceptable as it is likely that nobody is in the exam room if the lights have been off for 12 or more hours. In various embodiments the capacitor may store any amount of charge appropriate for the operation of lighting system 1400.

As previously described, using lighting structures as a sensor location may be advantageous because lighting structures are generally located at the center of an examination room, which may enable a transmitted wireless signal to maintain a general coverage of the examination room without extending beyond the walls of the examination room. Furthermore, lighting structures are generally centered about the patient. For example, lighting system 1400 may be adjusted by the physician to a desired location around a patient for a particular examination and/or operation procedure. Thus, the position of a medical professional and/or patient relative to lighting system 1400 may be closely correlated to the occurrence of an examination. According to various embodiments, medical personnel and/or patients are not required to login, check in, or do any extra work to indicate their presence in a room. Instead, their location is tracked based on the signals received at the various Bluetooth or Wi-Fi transceivers within lighting system 1400 to automatically manage scheduling. Furthermore, lighting system 1400 may provide added privacy protection for sensitive medical information protected by HIPAA.

Various other lighting systems that may be implemented with various embodiments of the present disclosure are further described in U.S. Patent Application No. 15/439,787 by Bullington et al., filed on Feb. 22, 2017, titled LIGHTING SYSTEM FOR MEDICAL APPOINTMENT PROGRESS TRACKING, which is incorporated by reference herein in its entirety and for all purposes.

In some embodiments, location sensor 1401 in lighting system 1400 may comprise a Wi-Fi extender, which may alternatively be referred to herein as a Wi-Fi booster or repeater. The Wi-Fi extender of sensor 1401 may be configured to connect to an existing wireless network and retransmit the signal corresponding to the size and other characteristics of a room, as previously described. For example, a medical-office may include a broadcast and multicast and/or unicast wireless network.

Figure 15:
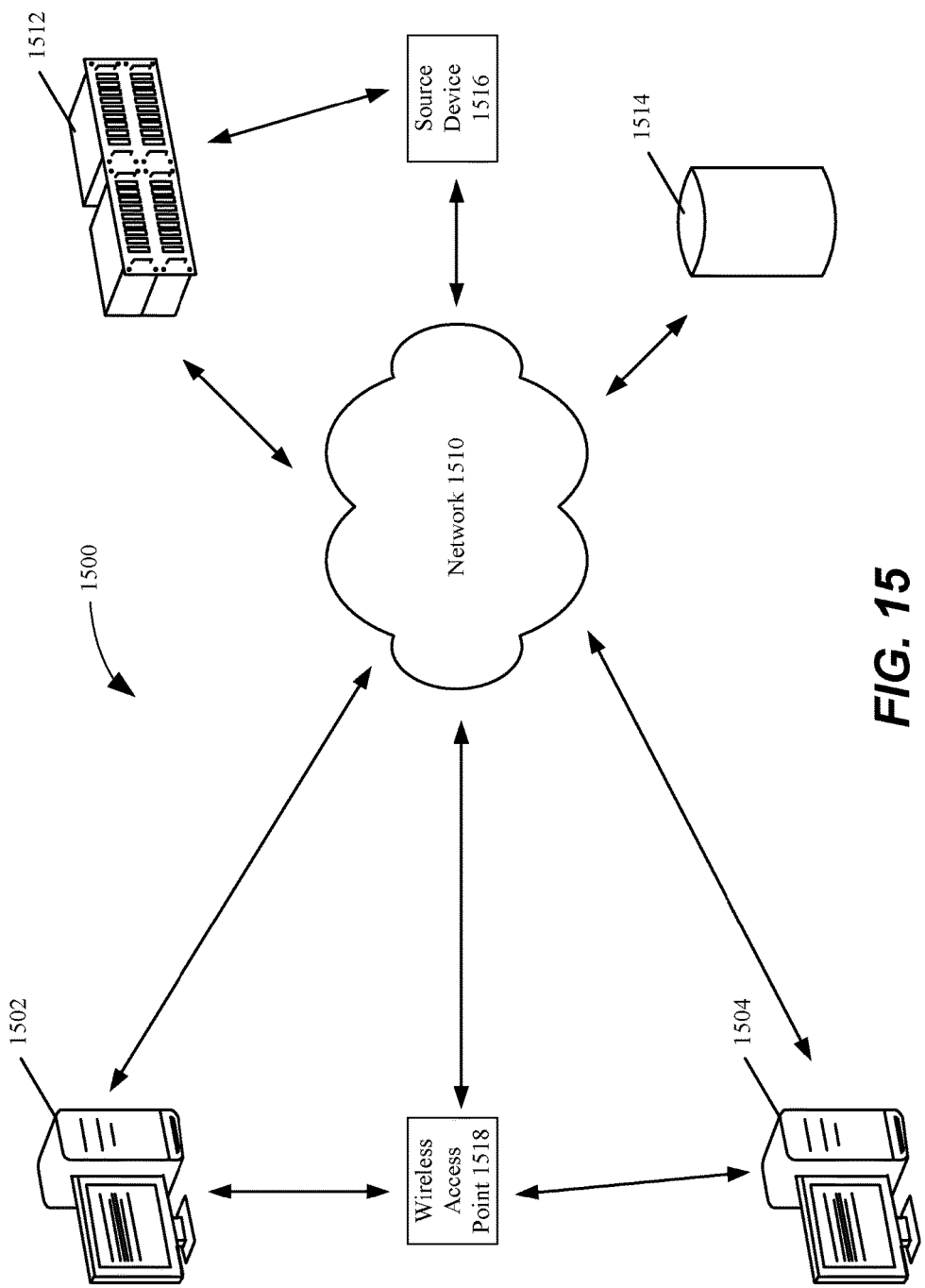
FIG. 15 illustrates an example network architecture 1500 that can be used in conjunction with the various techniques and embodiments of the present disclosure.

FIG. 15 illustrates an example network architecture 1500 that can be used in conjunction with the various techniques and embodiments of the present disclosure. In various embodiments, network architecture 1500 may be a broadcast and multicast/unicast system. The network architecture 1500 includes a number of user devices 1502 and 1504 communicably connected to server system 1512 by a network 1510.

In various embodiments, network 1510 may be a wired and/or wireless network. In some embodiments, network 1510 may be a local area network (LAN), which interconnects computers and devices within a limited area. In other embodiments, network 1510 may comprise other network types, such as a wide area network (WAN), or a global network, such as the Internet. In some embodiments, network 1510 may be an unsecured wireless network. However, in other embodiments, network 1510 may be a secure wireless network in which various devices and systems may require authorization to access network 1510. Various security protocols may be implemented to prevent unauthorized access to sensitive private medical information protected under HIPAA. Such secure network may implement various network protection protocols, including WEP, WPA, and WPA2.

In some embodiments, mobile device 1502 and/or 1504 may be a user ID, such as ID 211, ID, 221, or ID 231, as described with reference to FIG. 2A, and/or a medical professional mobile device 1301, as described with reference to FIG. 13. In some embodiments, mobile device 1502 includes multiple receivers for receiving both broadcast and multicast/unicast data, such as data from IP networks delivered over cellular, mobile, WiFi, etc. Although only two user devices are depicted in FIG. 15, it should be recognized that architecture 1500 may include any number of user devices corresponding to individuals, such as medical professionals and/or patients.

In some embodiments, server system 1512 may be schedule management system 1200 and/or medical scheduling management hub 1315. In some embodiments, server system 1512 includes one or more processors and memory. The processors of server system 1512 execute computer instructions (e.g., network computer program code) stored in the memory to perform functions of a network data exchange server.

As previously described, server system 1512 may function as a content server configured to receive and store network profile information, including appointment change status info 1141, patient appointment info 1101, and/or patient medical records 1115. Server system 1512 may also function as a dispatch server configured to transmit and/or route network data packets including network messages. In some embodiments, the network architecture 1500 may further include a database 1514 communicably connected to user devices 1502 and 1504, and server system 1512 via network 1510. In some embodiments, database 1514 may be database 1100. In some embodiments, network data, or other information such as appointment information and patient information may be stored in and/or retrieved from database 1514. In some embodiments, database 1514 is a component within server system 1512 and stored within memory of server system 1512. Although only one server system is depicted in FIG. 15, it should be recognized that architecture 1500 may include any number of server systems configured to perform one or more of the functionalities described above.

In various embodiments, network architecture 1500 includes a signal source device 1516. Source device 1516 may connect network 1510 with a global network such as the Internet. In some embodiments, source device 1516 may be a modem and/or router. In some embodiments source device 1516 may be a wireless router. In some embodiments, source device 1516 may wirelessly connect server system 1512 to network 1510. In some embodiments, source device 1516 may be a component within server system 1512.

In various embodiments, network architecture includes wireless access point (WAP) 1518. In some embodiments, one or more WAPs 1518 may be connected to a wired network and provide wireless access to the LAN. In some embodiments, user devices 1502 and 1504 may connect to network 1510 via wireless access point (WAP) 1518. WAP 1518 may be a networking hardware device that allows a Wi-Fi compliant device, such as user devices 1502 and 1504, to connect to network 1510. In some embodiments, WAP 1518 may connect to network 1510 via source device 1516, such as a router (via a wired or wireless network), as a standalone device. However, in some embodiments, WAP 1518 may be an integral component of source device 1516. In some embodiments WAP 1518 may be wirelessly connected to network 1510.

Users of the client devices 1502 and 1504 may access the server system 1512 to participate in a network data exchange service, such as a medical appointment scheduling service. For example, the client devices 1502 and 1504 can execute web browser applications that can be used to access the network data exchange service. In another example, the client devices 1502 and 1504 can execute software applications that are specific to the network (e.g., networking data exchange "apps" running on smartphones). In further embodiments, client devices 1502 and 1504 are configured to use global position system (GPS), or other geo-location capabilities, to determine a user's location.

Users interacting with the user devices 1502 and 1504 can participate in the network data exchange service provided by the server system 1512 by providing appointment requests and other patient related data. In some implementations, the client devices 1502 and 1504 can be computing devices such as laptop or desktop computers, smartphones, personal digital assistants, portable media players, tablet computers, or other appropriate computing devices that can be used to communicate with a network. In some implementations, the server system 1512 can include one or more computing devices such as a computer server. In some implementations, the server system 1512 can represent more than one computing device working together to perform the actions of a server computer (e.g., cloud computing). In some implementations, the network 1510 can be a public communication network (e.g., the Internet, cellular data network, dial up modems over a telephone network) or a private communications network (e.g., private LAN, leased lines).

In some embodiments the Wi-Fi extender of sensor 1401 may comprise two or more wireless routers. A first wireless router may be configured to connect to a wireless signal of an existing network, such as network 1510. The first wireless router may receive the wireless signal via source device 1516. For example, a Wi-Fi signal may be transmitted by source device 1516, such as a server, a mobile device, router, or another wireless access point on the wireless network. For example, transmitter/receiver 236, as depicted in FIG. 2A, may be a source device 1516 which transmits a wireless signal. As another example, schedule management system 1200 may include a source device 1516 which transmits a wireless signal.

The first wireless router may then transfer the wireless signal to a second wireless router in the Wi-Fi extender, which rebroadcasts that Wi-Fi signal into the room. In some embodiments, the Wi-Fi extender may function as a wireless access point 1518 to connect to user devices that are in range within the room. User devices, such as user IDs or medical professional mobile devices, may then connect to the network via the signal rebroadcasted by the Wi-Fi extender.

In some embodiments, the Wi-Fi extender may be a single band repeater, which receives, then retransmits each packet of data using the same radio on the same channel. However, in some embodiments, the Wi-Fi extender may be a dual band repeater, which may communicate with source device 1516 and rebroadcast on different channels. For example, the Wi-Fi extender may receive a wireless signal from a main router on lower channels and then rebroadcast the wireless signal on higher channels. As previously described, the wireless signal may be tuned to a strength and/or shape corresponding to the characteristics of the room.

In some embodiments, the Wi-Fi extender may be directly connected a network via a wired connection, such as via Ethernet. In some embodiments, the Wi-Fi extender of sensor 1401 may comprise a powerline adapter, such as a powerline Ethernet adapter, which is configured to receive a network signal sent from a router or other source device 1516 over electrical circuits. For example, a first adapter may be connected to a source device 1516, such as a router, via a direct wired connection, such as Ethernet. The first adapter may then be plugged into a power outlet coupled to an electrical circuit. The first adapter may be configured to transmit the network signal from the source device 1516 through the electrical circuit to a second powerline Ethernet adapter within location sensor 1401 of lighting system 1400, which is plugged into another power outlet coupled to the electrical circuit. The second adapter of location sensor 1401 may be configured to convert the signal to a wireless signal within the room to connect with user devices. As previously described, the wireless signal may be tuned to a strength and/or shape corresponding to the characteristics of the room.

As such, the network signal may travel with the same electrical current that powers lighting system 1400 along an electrical circuit from the power source to lighting system 1400. In some embodiments, the electrical current including the network signal may run directly from power supply 1413 to power interface 1415, which supplies the electrical current to lighting interface 1408. In some embodiments, the electrical current is used to power lighting element 1409 to emit light. As compared to a Wi-Fi extender comprising a plurality of wireless router, by transmitting the network signal through the electrical current via powerline adapters may add an additional level of security for the network. Because there the network signal is not transmitted to the room via wired connection, there is one less step of signal transmission that is done wirelessly. Therefore, the transmission of the signal to the Wi-Fi extender is direct and not subject to possible reception by other unauthorized devices. Furthermore, a direct transmission of a network signal via electrical current is more direct and immediate with less drop off in signal strength.

As previously described, lighting element 1409 may additionally function as an antenna to emit the network signal from the electrical current as a wireless signal. However, in some embodiments, lighting system 1400 may include a separate transmitter, such as transmitter 1419, configured to emit the network signal as a wireless signal. In some embodiments, lighting element 1409 may function as a broadcast and/or receiver antenna for transmitter 1419. Wireless signals, including data packets, received by lighting system 1400 may similarly be transmitted through the electrical circuit to the source device 1516 and/or to a server system. In this way, the same electrical current directed to lighting system 1400 may provide power to the lighting element 1409 and various other components of lighting system 1400, as well as the network signal. As such, the various components of lighting system 1400 depicted in FIG. 14 may have access to the network signal, which also provides continuous power.

In various implementations, the Wi-Fi extender of location sensor 1401 in a room may transmit information identifying the room such that a user device may identify the room location corresponding to the received signal. In some embodiments, each Wi-Fi extender the lighting system 1400 of a room includes a unique IP address and/or MAC address. Such information may be included within data packets transmitted through the wireless signal by the Wi-Fi extender.

According to various embodiments, data may be transmitted by the Wi-Fi extender over the wireless network that implements standards from the IEEE 802.11 standards family, such as Wi-Fi. Such data may be transmitted in the form of data packets corresponding to a seven-layer Open Systems Interconnection (OSI) model of computer networking and utilize standard protocols such as transmission control protocol (TCP) or user datagram protocol (UDP). A typical UDP data packet corresponding to an IEEE 802.11 wireless standard includes a media access control (MAC) sublayer of the data-link layer, organized as a MAC frame consisting of a MAC header, a frame body, and a frame check sequence (FCS) as further explained below in FIG. 16.

As previously explained, in some implementations, the wireless network is a secure wireless network. The data within the frame body of a data packet sent over a secure wireless network, called a payload, is encrypted and cannot be read by a user device that is not authorized to receive data packets on the secure wireless network. However, in some implementations, data packets may be sent via multicast format, such as IP multicast, application layer multicast, or multicast over other wireless networks. An example of an IP multicast technique may utilize one or more IP multicast group addresses as destination IP addresses that are stored in the MAC headers of the sent data packets. Such multicast data packets may be sent by the Wi-Fi extender via a wireless communication interface, such as transmitter 1419. In some embodiments, the destination IP addresses include MAC addresses reserved specifically for Ethernet multicast.

In other embodiments, the Wi-Fi extender may send a simple service discovery protocol (SSDP) to continuously scan for the presence of user devices. In some embodiments, the Wi-Fi extender may transmit multi-cast data packets 1620 when a user device has been detected. In other embodiments, the Wi-Fi extender may continuously transmit multicast data packets with information corresponding to the identification of the room. In some implementations, a user device may include hardware, such as a wireless interface, configured to scan for and receive multiple multicast data packets addressed to one or more IP multicast group addresses over a wireless network. In some embodiments, the user device may be set to an initial listening mode to actively search for wireless communications being sent on various communication channels. For example, 2.4 GHz Wi-Fi has 14 channels for communication, 11 of which are approved for use. When in listening mode, the user device spends a certain amount of time, such as 1 second, on each channel to detect for transmission. Once a transmission is detected on a particular channel, the user device may stay tuned to the particular channel to receive the sent multicast data packets.

In some embodiments, a user device may not have access to the secure wireless network when receiving the multicast data packets. For example, the Wi-Fi extender of lighting sensor 1400 may provide the same network protection as existing routers, such as WEP, WPA and WPA2. In other embodiments, the wireless connection device may not be authorized to access the secure wireless network and thus, cannot decrypt encrypted portions of the multicast data packets. By restricting access to the secure wireless network by a user device, the system may provide for additional network security, such as for HIPAA related information. In some embodiments, only user devices corresponding to certain individuals may be restricted. For example, user devices corresponding to patients may not have access to the secure network. However, in some embodiments, user devices corresponding to medical professionals may have access to the secure network.

Although a user device may not have access to the secure wireless network, the unauthorized wireless connection device may still receive and read the MAC addresses of multicast data packets sent over a secure wireless network. In some embodiments, the Wi-Fi extender may send out multiple multicast data packets to one or more specific destination IP addresses such that a source IP address associated with the Wi-Fi extender is mapped to one or more MAC addresses in the MAC frame of a data packet.

Figure 16:
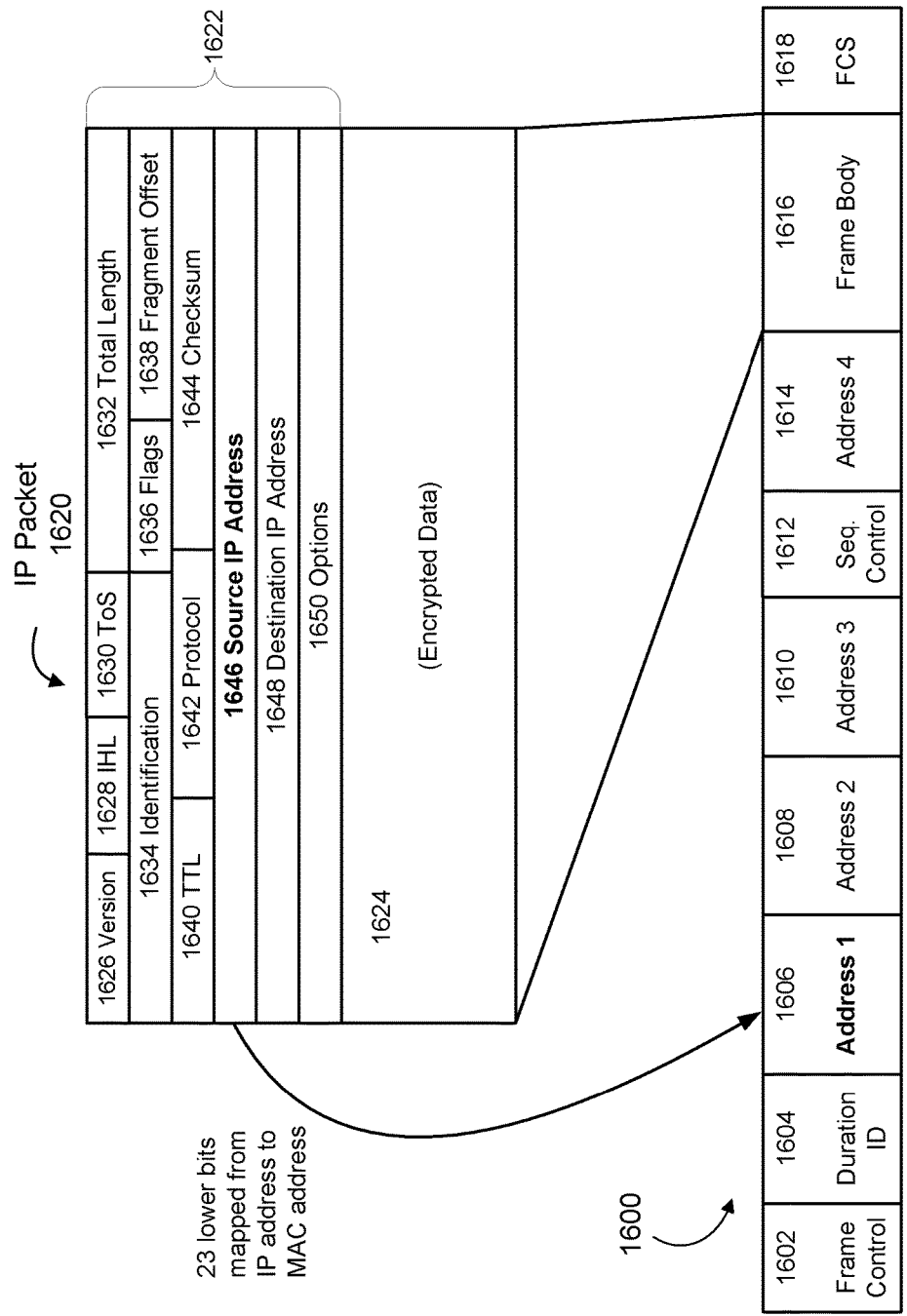
FIG. 16 illustrates an embodiment of a typical IEEE 802.11 MAC frame 1600 for a multicast data packet, in accordance with one or more embodiments.

With reference to FIG. 16, shown is an illustration of an embodiment of a typical IEEE 802.11 MAC frame 1600 for a multicast data packet, in accordance with one or more embodiments. Such multicast data packet may be transmitted by a wireless access point 1518, such as a Wi-Fi extender of location sensor 1401. MAC frame 1600 includes the following fields: frame control 1602, duration/ID 1604, sequence control 1612, frame body 1616, frame check sequence 1618, and MAC addresses 1606, 1608, 1610, and 1614. Frame body 1616 contains data and/or information organized as IP packet 1620. IP packet 1620 includes IP header 1622 and variable-length data field 1624. IP header 1622 consists of several fields including version 1626, internet header length (IHL) 1628, type of service (ToS) 1630, total length 1632, identification 1634, flags 1636, fragment offset 1638, time to live (TTL) 1640, protocol 1642, checksum 1644, source IP address 1646, destination IP address 1648, and options 1650. The data and/or information in data field 1624, also known as the "payload," is encrypted. In certain embodiments, the data and/or information in data field 1624 may be unencrypted. In certain embodiments, IP packet 1620 may not include one or more of the fields shown in FIG. 16, or may include one or more additional fields.

In some embodiments, source IP address 1646 may be a standard 162-bit address utilized in Internet Protocol version 4 (IPv4), and an address designated as Class D, which are reserved for multicast services. The lower 23 bits of source IP address 1646 may be directly mapped to MAC address 1606 in a hexadecimal base 16 format. In other embodiments, the source IP address 1646 may be directly mapped to any of the other MAC addresses in the MAC header, including 1608, 1610, and/or 1614. In some embodiments, a user device may receive multiple multicast packets when in range of the Wi-Fi extender of location sensor 1401 and identify the value of MAC address field 1606 of each packet to determine the corresponding room. In some embodiments, the user device may directly read the source IP address 1646.

According to various embodiments, the wireless connection device may include memory and a processor that is configured to identify the source IP address 1646 mapped to MAC address 1606 corresponding to the Wi-Fi extender in a particular room. In some embodiments, the location information may be sent to a server system, such as schedule management system 1200 or medical scheduling management hub 1315, for additional processing to identify the location of the individual corresponding to the user device, as well as to determine appointment scheduling changes. In some embodiments, the location information may also include duration of the wireless connection. In some embodiments, some of the processing of the location data may be performed at the user device. For example, the user device may identify the location of the individual corresponding to the user device and the start time and end time of the connection. In some embodiments, the user device may then record the location information In some embodiments, a user device may have access to the network. In other embodiments, the network may not be a secure network. In such instances, information corresponding to the identity of the room may be transmitted within the data field 1624 of the multicast IP packet 1620, which may be read by the user device.

In other embodiments, a user device may be configured to transmit data packets 1620 to lighting system 1400 when connected to the wireless signal broadcasted by the Wi-Fi extender. In some embodiments, the user device may continue to transmit data packets 1620 when in range of the wireless signal transmitted by the Wi-Fi extender. In other embodiments, the user device may send a simple service discovery protocol (SSDP) to continuously scan for the presence of Wi-Fi extenders and/or other wireless access points 1518. In some embodiments, the user device may transmit multi-cast data packets 1620 when a Wi-Fi extender of a lighting system has been detected. In other embodiments, the user device may continuously transmit multicast data packets with information corresponding to the identification of the user device and/or corresponding individual.

Such data packets may include source IP address information 1646 and/or MAC address information 1648 corresponding to that user device. Such data packets 1620 may be received at lighting system 1400 at a wireless interface, such as by medical professional mobile device interface 1421. In some embodiments, processor 1405 of lighting system 1400 may be configured to determine the identity of the individual corresponding based upon the source IP address 1646 and/or MAC address information 1648. In some embodiments processor 1405 may further record the duration of the connection. In some embodiments, the location information is transmitted to a server system, such as schedule management system 1200 and/or medical scheduling management hub 1315, by lighting system 1400 via an interface, such as notification hub interface 1411, for processing to determine appointment scheduling changes. However, in some embodiments, the data packets 1620 received from a user device may be sent directly to a server system for processing to determine the identity and location of the individual corresponding to the user device, as well as to determine appointment scheduling changes.

Figure 17A:
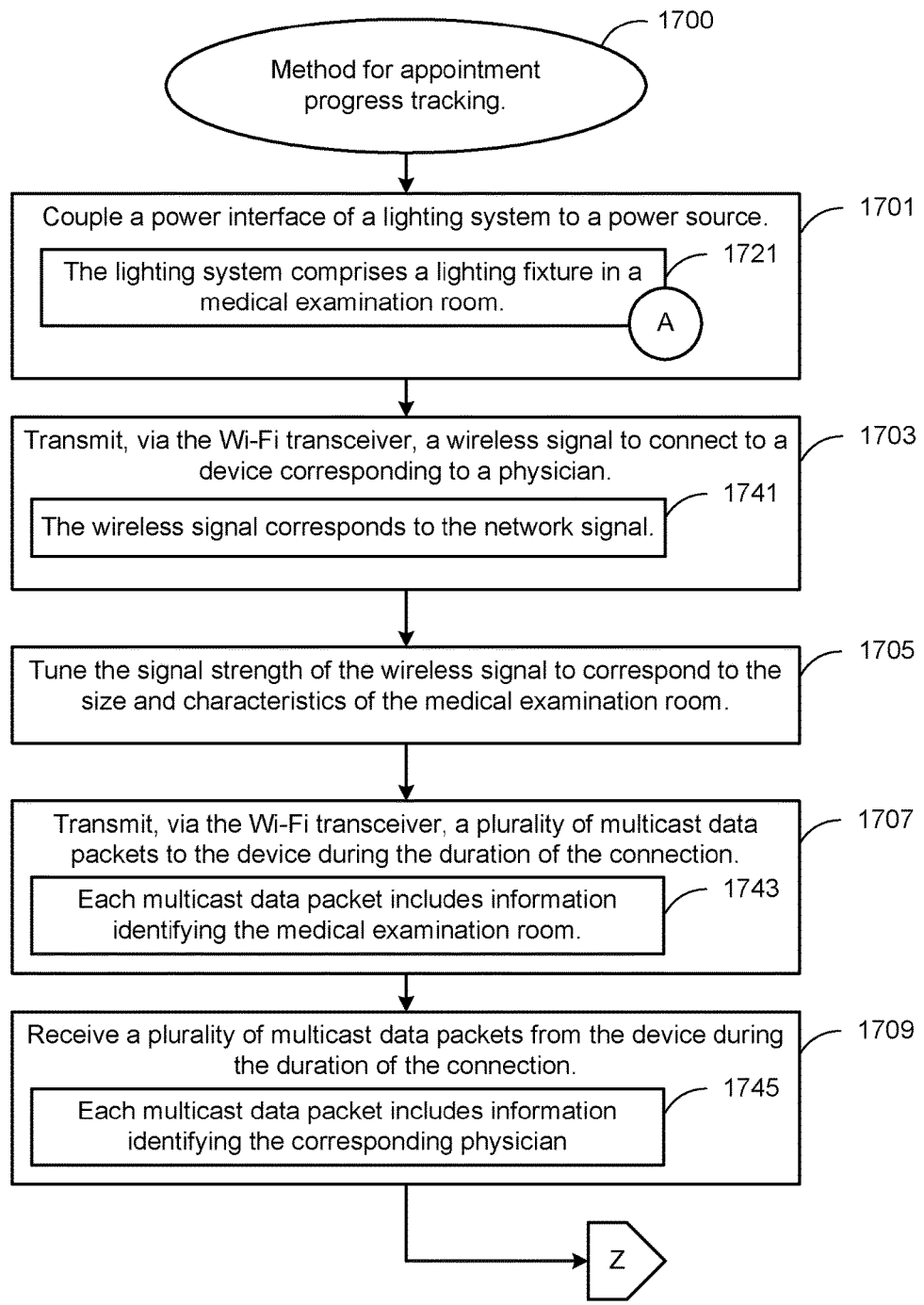
FIGS. 17A-17C illustrates an example method 1700 for appointment progress tracking, in accordance with one or more embodiments.
Figure 17B:
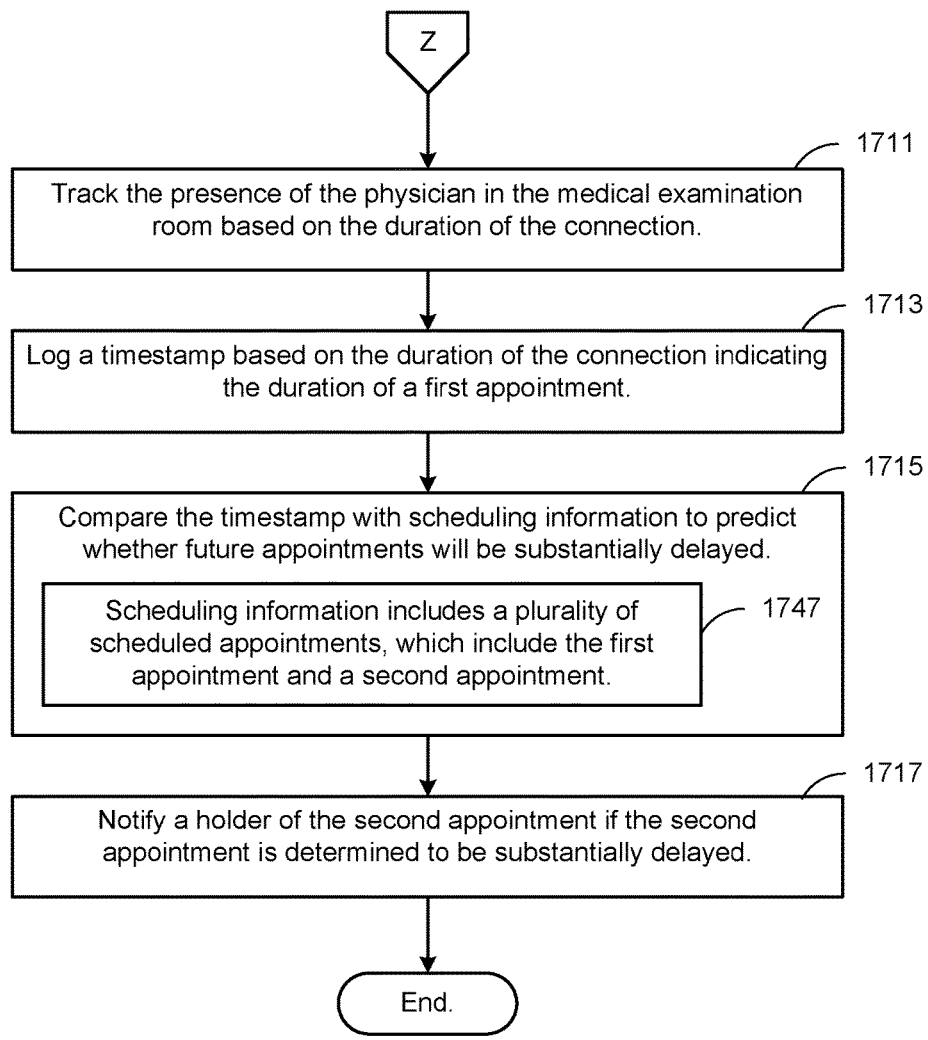
Figure 17C:
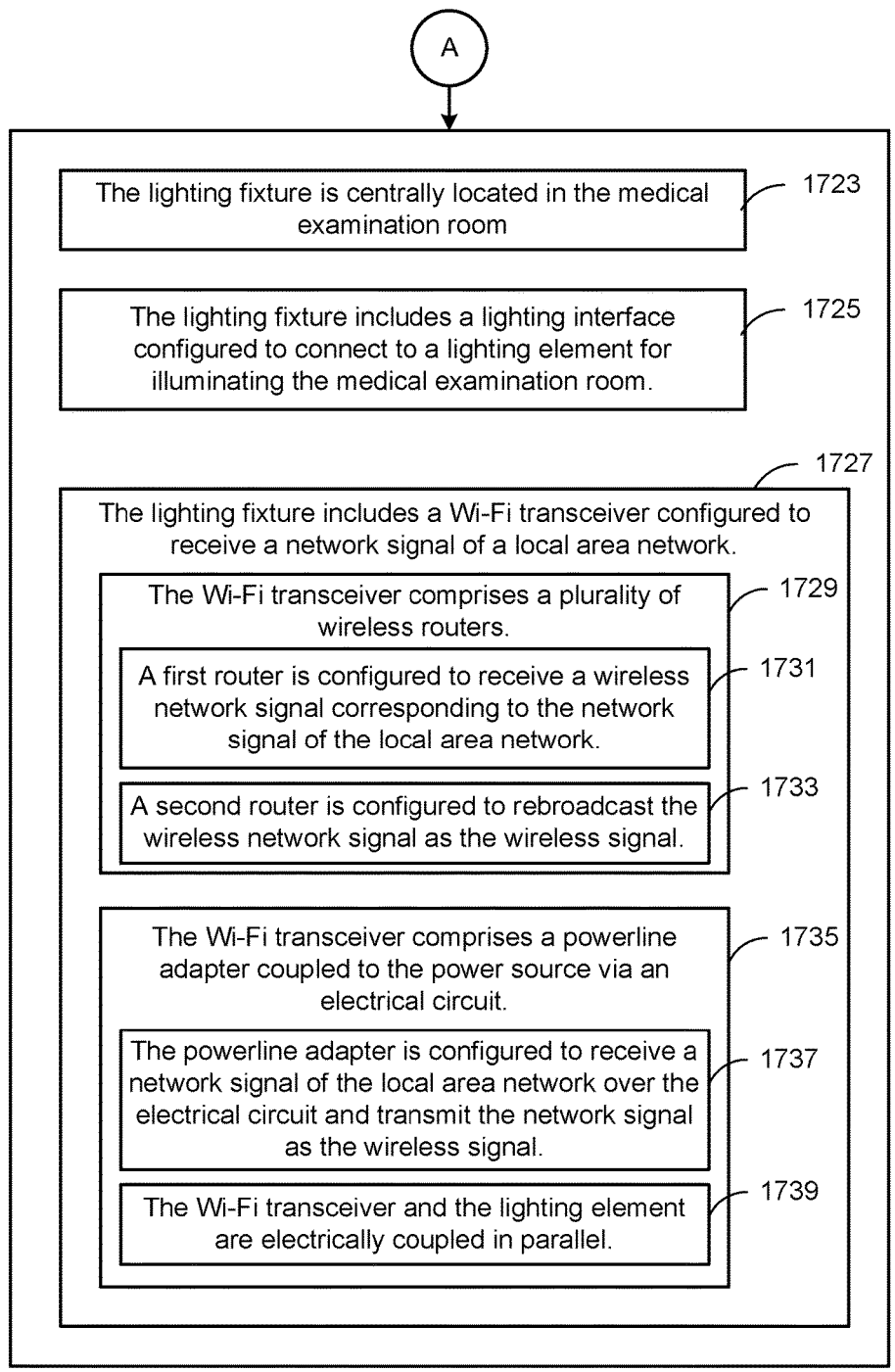

With reference to FIGS. 17A-17C, shown is an example method 1700 for appointment progress tracking, in accordance with one or more embodiments. In various embodiments, method 1700 may be a method for medical appointment progress tracking for improving patient wait times for medical appointments, as previously described in the present application. At operation 1701, a power interface of a lighting system 1721 is coupled to a power source. In some embodiments, a power source may be an electrical circuit, such as electrical circuit 1737, which is further described below.

In some embodiments, the lighting system 1721 may be lighting system 1400. In some embodiments, the lighting system 1721 comprises a lighting fixture 1723 in a medical examination room. As previously described, the lighting fixture 1723 may be centrally located in the medical examination room. In some embodiments, the lighting fixture 1723 may be mounted on the ceiling at the center of the examination room. In other embodiments, the lighting fixture 1723 may be adjustable such that the position of lighting system 1723 may be moved around a patient and/or an examination area for illumination of desired areas of the patient and/or examination area.

In some embodiments, the lighting fixture 1723 includes a lighting interface configured to connect to a lighting element 1725 for illuminating the medical examination room. In various embodiments, lighting element 1725 may be lighting element 1413. As previously described, lighting interfaces may comprise a base with terminals for transferring electrical power to a lighting element 1725 comprising a wire filament. In other embodiments, a lighting interface may comprise anode and cathode leads to provide electrical current to a lighting element 1725 comprising one or more LEDs. In yet further embodiments, where a lighting element 1725 comprises a light bulb, a lighting interface may comprise one or more various light bulb couplings, such as a standard Edison screw coupling.

In some embodiments, the lighting fixture 1723 also includes a Wi-Fi transceiver 1727 configured to receive a network signal of a local area network. In various embodiments, Wi-Fi transceiver 1727 may be a location sensor, such as location sensor 1401, which comprises a Wi-Fi extender. Other signal transceivers may be implemented in various embodiments, such as Bluetooth or infrared signals.

In various embodiments, Wi-Fi transceiver 1727 may be configured to connect to an existing network signal and wirelessly transmit the network signal into the examination room. As such, a wireless signal 1741 is transmitted, via the Wi-Fi transceiver 1727, to connect to a device corresponding to a physician at 1703. The wireless signal 1741 may correspond to the network signal of the local area network. In some embodiments, the device may be a user device, such as an ID tag (e.g., ID tags 211, 221, and 231) and/or a medical professional mobile device 1301.

In some embodiments, the Wi-Fi transceiver 1727 may connect to the existing network signal of the local area network wirelessly. For example, in certain implementations, the Wi-Fi transceiver 1727 comprises a plurality of wireless routers 1729. A first router 1731 may be configured to receive a wireless network signal corresponding to the network signal of the local area network. A second router 1733 may be configured to rebroadcast the wireless network signal as the wireless signal 1741.

In some embodiments, the Wi-Fi transceiver 1727 may connect to the existing network signal of the local area network through a wired connection. For example, the Wi-Fi transceiver 1727 may be connected to a network source, such as a router or modem, via Ethernet cable. As another example, in other implementations, the Wi-Fi transceiver 1727 comprises a powerline adapter 1735 coupled to the power source via an electrical circuit 1737. The powerline adapter 1735 may be configured to receive the network signal of the local area network over the electrical circuit 1737 and transmit the network signal as the wireless signal 1741. The Wi-Fi transceiver 1735 and the lighting element 1725 may be electrically coupled (1739) in parallel.

At 1705, the signal strength of the wireless signal 1741 is tuned to correspond to the size and characteristics of the medical examination room, such as via amplifier 1417. As previously described, a the transmission power of Wi-Fi transceiver 1727 may be decreased for a smaller examination room, such that the signal range of the transmitted wireless signal 1741 is shortened and does not extend beyond the walls of the examination room. Alternatively, the transmission power of Wi-Fi transceiver 1727 may be increased for a larger examination room, such that the signal range of the transmitted wireless signal 1741 is extended up to, but not beyond the walls of the examination room. In various embodiments, unidirectional antennas may be implemented to create a signal range of a desired shape to correspond to the characteristics of a given room.

At 1707, a plurality of multicast data packets 1743 are transmitted via the Wi-Fi transceiver 1727 to the device during the duration of the connection. Each multicast data packet 1743 may include information identifying the medical examination room. As previously described, the payload of each data packet 1743 may include information identifying the corresponding examination room, in which the Wi-Fi transceiver 1727 is located in. Such information may be received and identified by a user device with access to the local area network, which may be a secure network.

As also previously described, each Wi-Fi transceiver 1727 may have a unique IP address. Each unique IP address may be associated with the corresponding examination room in which the Wi-Fi transceiver 1727 is located in. The IP address may be located in the source IP address field 1646 and/or one or more MAC address fields, such as MAC address 1606. A user device that receives multicast data packets 1743 may process and identify the examination room based on the source IP address and/or MAC address even if it does not have access to a secure network.

In some embodiments, data packets 1743 including such information may additionally, and/or alternatively, be sent to a server system such as schedule management system 1200 or medical scheduling management hub 1315 for identification of the examination room.

At 1709, a plurality of multicast data packets 1745 are received from the device during the duration of the connection. Each multicast data packet 1745 may include information identifying the corresponding physician. In some embodiments, such information may identify another individual corresponding to the device, such as a medical professional or patient. Each user device that transmits data packets over Wi-Fi may include a unique IP address. As in step 1707, the unique IP address may be located in the source IP address field 1646 and/or one or more MAC address fields of multicast data packets 1745 transmitted by a user device. Lighting system 1721 may receive such information to identify the device, and the corresponding individual (such as a physician, medical professional, or patient), that has formed a connection. Information identifying the corresponding individual may additionally, and/or alternatively, be included in the payload of a data packet 1745.

In some embodiments, data packets 1745 including such information may additionally, and/or alternatively, be sent to a server system such as schedule management system 1200 or medical scheduling management hub 1315 for identification of the corresponding individual.

At 1711, the presence of the physician in the medical examination room is tracked based on the duration of the connection, such as previously described in FIGS. 4A-4C and FIG. 6. For example, a timestamp may be logged based on the duration of the connection indicating the duration of a first appointment, at 1713. As previously described a processor may be configured to record when the connection is first made between the Wi-Fi transceiver 1727 and the device. The processor may be processor 1405 in lighting system 1400. In other embodiments, the processor may be processor 1205 and/or 1307. In various embodiments, the connection may be recorded by a timestamp. A timestamp may be logged at the time a connection is made between the Wi-Fi transceiver 1727 and the device. In some embodiments, the time a connection is made may be determined based on when the Wi-Fi transceiver 1727 begins receiving data packets 1745 transmitted from the device, and/or when the device begins receiving data packets 1743 transmitted from the Wi-Fi transceiver 1727. A timestamp may also be logged at the time the connection between the Wi-Fi transceiver 1727 and the device is terminated. In some embodiments, the time a connection is terminated may be determined based on when the Wi-Fi transceiver 1727 stops receiving data packets 1745 transmitted from the device, and/or when the device stops receiving data packets 1743 transmitted from the Wi-Fi transceiver 1727.

At 1715, the timestamp is compared with scheduling information 1747 to predict whether future appointments will be substantially delayed, such as in step 611 previously described with reference to FIG. 6. In some embodiments, scheduling information 1747 includes a plurality of scheduled appointments, which include the first appointment and a second appointment. At 1717, a holder of the second appointment is notified if the second appointment is determined to be substantially delayed, such as in step 623.

Figure 18:
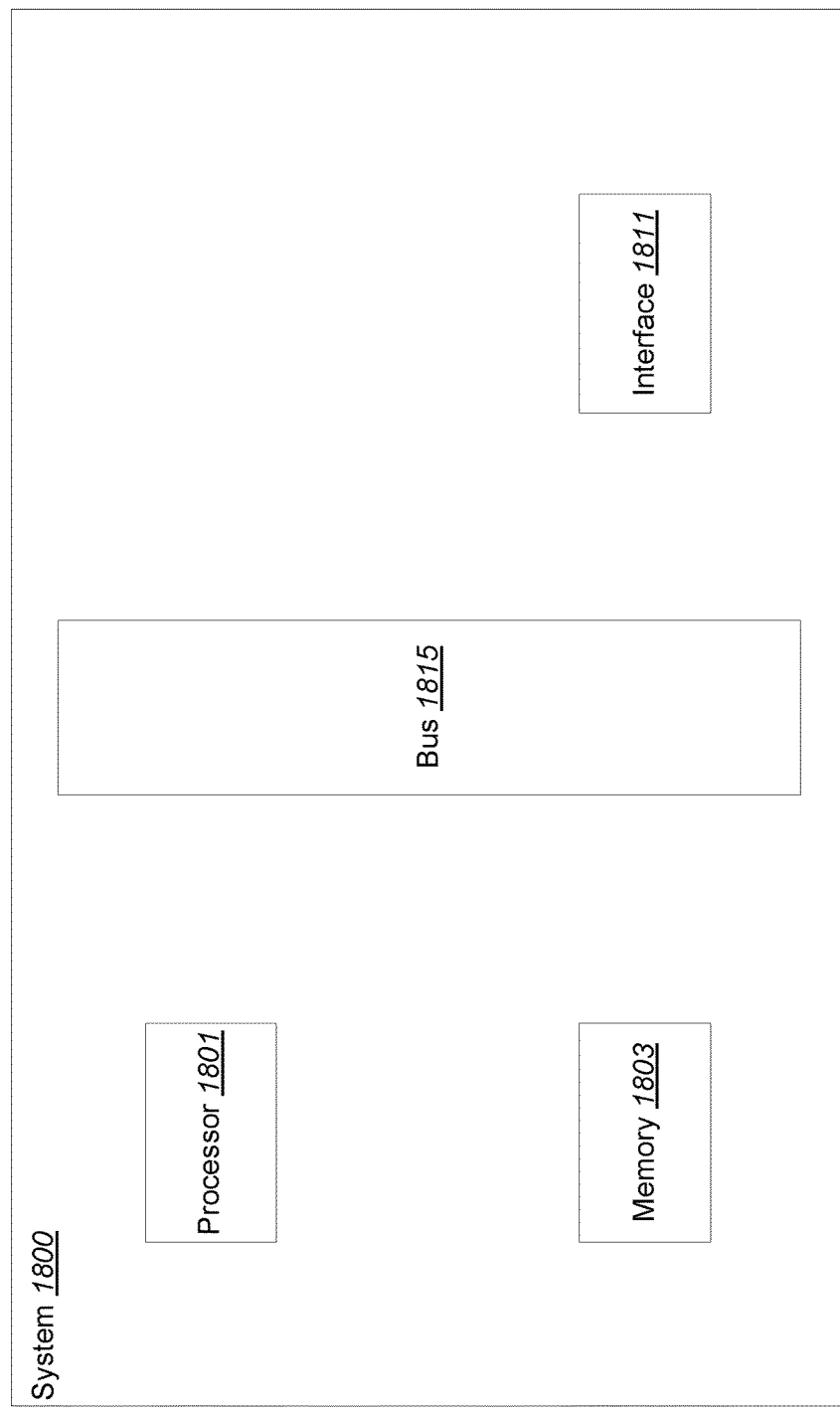
FIG. 18 is an example of a computer system that can be used with various embodiments of the present disclosure.

Various computing devices can implement the methods and systems described. For instance, a mobile device, computer system, etc. can be used to generate artificially rendered images. With reference to FIG. 18 shown is a particular example of a computer system that can be used to implement particular examples of the present disclosure. According to particular example embodiments, a system 1800 suitable for implementing particular embodiments of the present disclosure includes a processor 1801, a memory 1803, an interface 1811, and a bus 1815 (e.g., a PCI bus or other interconnection fabric) and operates as a streaming server. The interface 1811 may include separate input and output interfaces, or may be a unified interface supporting both operations.

In some embodiments, processor 1801 may be processors 1205, 1307, 1317, and/or 1405. When acting under the control of appropriate software or firmware, the processor 1801 is responsible for processing, modifying, transmitting, and/or receiving data packets, such as data packets 1743 and/or 1745, to a user device, such IDs 211, 221, and 231, and/or medical professional mobile device 1301, such as in steps 1707 and 1709. In other embodiments, processor 1801 is responsible for receiving data packets sent by a user device and/or lighting system, as well as reading the MAC addresses and/or other portions of such data packets as described in FIG. 16. Various specially configured devices can also be used in place of a processor 1801 or in addition to processor 1801. The complete implementation can also be done in custom hardware.

The interface 1811 is typically configured to send and receive data packets or data segments over a network. Particular examples of interfaces the device supports include Ethernet interfaces, frame relay interfaces, cable interfaces, DSL interfaces, token ring interfaces, and the like. In some embodiments, interface 1811 may be location sensor 1401 and/or transmitter 1419. In some embodiments, interface 1811 may be interfaces 1207, 1211, and/or 1213 in schedule management system 1200. In some embodiments, interface 1811 may be interfaces 1311, 1321, and/or 1325 in medical appointment delay notification system 1300.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the system 1800 uses memory 1803 to store data and program instructions and maintained a local side cache. The program instructions may control the operation of an operating system and/or one or more applications, for example. The memory or memories may also be configured to store received metadata and batch requested metadata. In some embodiments, memory 1803 may be memory 1203, 1305, 1319, and/or 1403.

According to various embodiments, the system 1800 is a server that also includes a transceiver, streaming buffers, and memory. The server may also be associated with configuration management, logging and report generation, and monitoring capabilities. Particular embodiments, functionality for allowing operation with mobile devices such as cellular phones operating in a particular cellular network and providing subscription management. According to various embodiments, an authentication module verifies the identity of devices including mobile devices. A logging and report generation module tracks mobile device requests and associated responses. A monitor system allows an administrator to view usage patterns and system availability. According to various embodiments, the fragment server handles requests and responses for media content related transactions while a separate streaming server provides the actual media streams.

Because such information and program instructions may be employed to implement the systems/methods described herein, the present disclosure relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the disclosure. It is therefore intended that the disclosure be interpreted to include all variations and equivalents that fall within the true spirit and scope of the present disclosure. Although many of the components and processes are described above in the singular for convenience, it will be appreciated by one of skill in the art that multiple components and repeated processes can also be used to practice the techniques of the present disclosure.

What is claimed is:

1. An apparatus comprising:
    a lighting interface configured to connect to a lighting element for illuminating a medical examination room, the medical examination room including a size;
    a power interface coupled to a power source; and
    a Wi-Fi transceiver configured to transmit a wireless signal to connect to a device for a duration,
        wherein the device corresponds to a physician, and
        wherein the wireless signal corresponds to a local area network;
        wherein the length of the duration of the connection is used to track the presence of the physician in the medical examination room;
        wherein the Wi-Fi transceiver is tuned to transmit a signal strength corresponding to the size and characteristics of the medical examination room; and
        wherein the apparatus is located in a lighting fixture in the medical examination room.

2. The apparatus of claim 1, wherein the lighting fixture is centrally located in the medical examination room.

3. The apparatus of claim 1, wherein the Wi-Fi transceiver is configured to transmit a plurality of multicast data packets to the device during the duration of the connection, each multicast data packet including information identifying the medical examination room.

4. The apparatus of claim 1, wherein the Wi-Fi transceiver is configured to receive a plurality of multicast data packets from the device during the duration of the connection, each multicast data packet including information identifying the corresponding physician.

5. The apparatus of claim 1, wherein the apparatus is configured to log a timestamp based on the duration of the connection indicating the duration of a first appointment.

6. The apparatus of claim 5, wherein the apparatus is further configured to compare the timestamp with scheduling information to predict whether future appointments will be substantially delayed, wherein scheduling information includes a plurality of scheduled appointments, the plurality of scheduled appointments including the first appointment and a second appointment.

7. The apparatus of claim 6, wherein the apparatus is further configured to notify a holder of the second appointment if the second appointment is determined to be substantially delayed.

8. The apparatus of claim 1, wherein the Wi-Fi transceiver comprises a plurality of wireless routers,
    wherein a first router is configured to receive a wireless network signal corresponding to the network signal of the local area network, and
    wherein a second router is configured to rebroadcast the wireless network signal as the wireless signal.

9. The apparatus of claim 1, wherein the Wi-Fi transceiver comprises a powerline adapter coupled to the power source via an electrical circuit,
    wherein the powerline adapter configured to receive the network signal of the local area network over the electrical circuit and transmit the network signal as the wireless signal;
    wherein the Wi-Fi transceiver and the lighting element are electrically coupled in parallel.

10. A system comprising:
    a lighting fixture in a medical examination room; and
    a location tracker located in the lighting fixture, the location tracker comprising:
        a lighting interface configured to connect to a lighting element for illuminating a medical examination room, the medical examination room including a size;
        a power interface coupled to a power source; and
        a Wi-Fi transceiver configured to transmit a wireless signal to connect to a device for a duration,
            wherein the device corresponds to a physician, and
            wherein the wireless signal corresponds to a local area network;

wherein the length of the duration of the connection is used to track the presence of the physician in the medical examination room, wherein the Wi-Fi transceiver is tuned to transmit a signal strength corresponding to the size and characteristics of the medical examination room.

11. The system of claim 10, wherein the lighting fixture is centrally located in the medical examination room.

12. The system of claim 10, wherein the Wi-Fi transceiver is configured to transmit a plurality of multicast data packets to the device during the duration of the connection, each multicast data packet including information identifying the medical examination room.

13. The system of claim 10, wherein the Wi-Fi transceiver is configured to receive a plurality of multicast data packets from the device during the duration of the connection, each multicast data packet including information identifying the corresponding physician.

14. The system of claim 10, wherein the apparatus is configured to log a timestamp based on the duration of the connection indicating the duration of a first appointment.

15. The system of claim 14, wherein the system is further configured to compare the timestamp with scheduling information to predict whether future appointments will be substantially delayed, wherein scheduling information includes a plurality of scheduled appointments, the plurality of scheduled appointments including the first appointment and a second appointment.

16. The system of claim 10, wherein the Wi-Fi transceiver comprises a plurality of wireless routers,
wherein a first router is configured to receive a wireless network signal corresponding to the network signal of the local area network, and
wherein a second router is configured to rebroadcast the wireless network signal as the wireless signal.

17. The system of claim 10, wherein the Wi-Fi transceiver comprises a powerline adapter coupled to the power source via an electrical circuit,
wherein the powerline adapter configured to receive the network signal of the local area network over the electrical circuit and transmit the network signal as the wireless signal;
wherein the Wi-Fi transceiver and the lighting element are electrically coupled in parallel.

18. A method for appointment progress tracking, the method comprising:
coupling a power interface of a lighting system to a power source, wherein the lighting system comprises:
a lighting fixture in a medical examination room, the lighting fixture including:
a lighting interface configured to connect to a lighting element for illuminating the medical examination room, the medical examination room including a size, and
a Wi-Fi transceiver configured to receive a network signal of a local area network;
transmitting, via the Wi-Fi transceiver, a wireless signal to connect to a device for a duration, wherein the device corresponds to a physician, and
wherein the wireless signal corresponds to the network signal;
tuning the signal strength of the wireless signal to correspond to the size and characteristics of the medical examination room; and
tracking the presence of the physician in the medical examination room based on the length of the duration of the connection.

19. The method of claim 18, further comprising transmitting, via the Wi-Fi transceiver, a plurality of multicast data packets to the device during the duration of the connection, each multicast data packet including information identifying the medical examination room.

20. The method of claim 18, further comprising receiving a plurality of multicast data packets from the device during the duration of the connection, each multicast data packet including information identifying the corresponding physician.

\* \* \* \* \*